US005206163A

United States Patent [19]

[11] Patent Number: 5,206,163

[45] Date of Patent: Apr. 27, 1993

Renard et al.

[54] DNA ENCODING BOVINE DIARRHEA VIRUS PROTEIN

[75] Inventors: Andre Renard, Beaufays, Belgium; Dino Dina, San Francisco, Calif.; Joseph Martial, Esneux, Belgium

[73] Assignee: Chiron Corporation, Emeryville, Calif.

[21] Appl. No.: 550,816

[22] Filed: Jul. 6, 1990

Related U.S. Application Data

[63] Continuation of Ser. No. 331,037, Mar. 29, 1989, abandoned, which is a continuation of Ser. No. 752,981, Jul. 8, 1985, abandoned.

[51] Int. Cl.[5] .......................... C12N 5/10; C12N 1/19; C12N 1/21; C12N 15/40

[52] U.S. Cl. .............................. 435/240.2; 435/252.3; 435/252.33; 435/256; 435/320.1; 536/23.72; 536/24.32; 536/23.4

[58] Field of Search ................. 536/27; 435/256, 69.1, 435/240.2, 71.1, 243, 172.1, 252.3, 172.3, 320.1, 235.1, 252.33

[56] References Cited

FOREIGN PATENT DOCUMENTS 0236977 9/1987 European Pat. Off. .

OTHER PUBLICATIONS

Gallitelli et al (1985) J. Virol. Meth. 11:141-144.

Purchio et al. (1984) J. Virology 52: 973-75.

Boere, et al., *J. Virol.* (1984) 52(2):572-582.

Fernelius, et al., *Am. J. Vet. Res.* (1971) 32(12):1963-1979.

Horzinek, *Non-Arthropod-borne Togaviruses* (1981) Academic Press, London pp. 1-11 and 23-39.

Porterfield, "The Togavirions. Biology, Structure, Replication," W. Schlesinger, ed. (1980) Academic Press, pp. 17-24.

Saurat, et al., "La Maladie des Muqueuses" (1972) *L'Expansion Scientific Francaise* Paris, pp. 229-251.

Renard, et al., *DNA* (1985) 4(6):429-438.

Smith, et al., *Proc. Natl. Acad. Sci.* (1983) 80:7155-7159.

"Les Multiples Formes Cliniques Ou Cachees De L'Infection Par Le Virus BVD", *Mall Magazine* Trimestriel Aout (Sep./Oct. 1984) E. R.: R. Ketels, pp. 1-11.

Kennedy, "The Togaviruses" (1984) Academic Press, Inc., Chapter 11, pp. 343-369.

Schlesinger, et al., "The Togaviruses" (1984) Academic Press, Inc., Chapter 13, pp. 371-392.

Russel, et al., "The Togaviruses" (1984) Academic Press, Inc., Chapter 18, pp. 503-529.

Westaway, et al., "The Togaviruses" (1984) Academic Press, Inc., Chapter 19, pp. 542-565.

*Primary Examiner*—Richard A. Schwartz

*Assistant Examiner*—Philip W. Carter

*Attorney, Agent, or Firm*—Barbara G. McClung; Kate H. Murashige

[57] ABSTRACT

The nucleotide sequence of the genome for bovine diarrhea virus (BDV) is disclosed. The sequence permits design and construction of vaccines effective against BDV.

10 Claims, 20 Drawing Sheets

```
---  -------  ----  --------  ------  -----  -----  ------------
     stul       xhol  pstl      bstE2  pstl  sacl  ava3
     mstII       sphl
       nhel

-------  -------  --  -  -  --  ----------------  -   --  -----------
        bgll     ball    pstl                        xbal   ndel
                   ball    sspl                        hpal
                   tthIII1-2                            aflll
                     nhel

---------  --  --  -  -------------       --------------  -------
          pvull    bglll            pstl  aatII             stul
          tthIII1-2                    bstXI
             bstXI                       ball
                bcll

--------------  ----  --  -------  --------------  --  --  --  -------
                ndel     sspl     aatII             narl   spel
                xmnl                                  bcll   apal
                     avr2

--------  ---------------  ----   ----------  -----  --------  ---
        apal              tthIII1-2         sphl   xma3      mstII
                               bglll
                                ecor5

  -  -  --  -   --  ------  ----------  --------  -------------------
  bglll  nael        kpnl        hpal      ecorl
avr2    xmnl  sall
 xbal      pvull
 avr2
     bstXI

--  --  --  ------------  --------------------  -----  -  -  ---  ---
  pvull                 ecorl                 stul  tthIII1-1
  tthIII1-2             mstII                         tthIII1-2
     aflll                                              tthIII1-1
        ndel                                                pvull

-  ----------------  -   ---------  -   -----------  --  -----------
 bcll               bsml          ava3             nhel            xmnl
                      ecor5         bglll             tthIII1-1
                       hindlll        bglll
                        bcll

-------  -----  ----  -----  -----  ----  ------  --------------
       tthIII1-2  xmnl    xmnl    hindlll     stul
             xmnl  bstE2  hindlll    bstE2    hpal
```

FIG.2A

```
------------  ------------------- --- ---  --- ------------
            ecor5                 bgl11   bgl1
             sca1                     spe1      tthIII1-1
                                           bstE2

--------  ---- --------------- ----  ------------ ---- ---
        nde1  bamh1           bgl11  sca1        bal1    stu1
         stu1                      pst1              bgl11
                                    xba1                 spe1

- - - -- - ---  ------ ------ -  ----------------- -- ----
    kpn1      bamh1   hind111  kpn1               ecor5
 ssp1    bal1   bstXI         bal1                 bal1
           sph1                  nde1                 xmn1
   cla1    hpa1

-- ---------- --
  pvu11      aatII
             nco1
```

1 ATGTATACGAGAATTTGCCTAACCTCGTATACATATTGGGCATTCTAAAAATAAATTAGGCC
CATATGCTCTTAAACGGATTGGAGCATATGTATAACCCGTAAGATTTTTATTTAATCCGG 58 stu1, 61 mstII, 63 TAAGGGACAAATCCTCCTTAGCGAAGGCCGAAAAGAGGCTAGCCATGCCCTTAGTAGGAC
ATTCCCTGTTTAGGAGGAATCGCTTCCGGCTTTTCTCCGATCGGTACGGGAATCATCCTG 100 nhe1, 123 TAGCAAAACAAGGAGGGTAGCAACAGTGGTGAGTTCGTTGGATGGCTGAAGCCCTGAGTA
ATCGTTTTGTTCCTCCCATCGTTGTCACCACTCAAGCAACCTACCGACTTCGGGACTCAT 183 CAGGGTAGTCGTCAGTGGTTCGACGCTTCGTGTGACAAGCCTCGAGGTGCCACGTGGACG
GTCCCATCAGCAGTCACCAAGCTGCGAAGCACACTGTTCGGAGCTCCACGGTGCACCTGC 223 xho1, 243 AGGGCATGCCCACAGCACATCTTAACCTGAGCGGGGGTCGTTCAGGTGAAAGCGGTTTAA
TCCCGTACGGGTGTCGTGTAGAATTGGACTCGCCCCCAGCAAGTCCACTTTCGCCAAATT 246 sph1, 303 CCAACCGCTACGAATACAGCCTGATAGGGTGCTGCAGAGGCCCACTGTATTGCTACTAAA
GGTTGGCGATGCTTATGTCGGACTATCCCACGACGTCTCCGGGTGACATAACGATGATTT 334 pst1, MetGluLeuIleThrAsnGluLeuLeuTyrLysThrTyr
363 AATCTCTGCTGTACATGGCACATGGAGTTGATTACAAATGAACTTTTATACAAAACATAC
TTAGAGACGACATGTACCGTGTACCTCAACTAATGTTTACTTGAAAATATGTTTTGTATG LysGlnLysProAlaGlyValGluGluProValTyrAsnGlnAlaGlyAspProLeuPhe
423 AAACAAAAACCCGCTGGAGTGGAGGAACCAGTATATAACCAAGCAGGTGACCCTTTGTTT
TTTGTTTTTGGGCGACCTCACCTCCTTGGTCATATATTGGTTCGTCCACTGGGAAACAAA 468 bstE2,

FIG.2B

```
    GlyGluArgGlyValValHisProGlnAlaThrLeuLysLeuProHisLysArgGlyGlu
483 GGCGAGAGAGGAGTGGTTCATCCGCAGGCGACGCTAAAACTGCCACATAAAAGAGGGGAG
    CCGCTCTCTCCTCACCAAGTAGGCGTCCGCTGCGATTTTGACGGTGTATTTTCTCCCCTC

    ArgGluValProThrAsnLeuAlaSerLeuProLysArgGlyAspCysArgSerGlyAsn
543 CGCGAAGTACCTACTAATCTGGCGTCTCTGCCAAAAAGAGGTGACTGCAGGTCGGGTAAC
    GCGCTTCATGGATGATTAGACCGCAGAGACGGTTTTTCTCCACTGACGTCCAGCCCATTG
                                                ^
    587 pstl,

    SerLysGlyProValSerGlyIleTyrLeuLysProGlyProLeuPheTyrGlnAspTyr
603 AGCAAGGGACCCGTGAGTGGAATCTACCTGAAACCGGGGCCGTTATTCTACCAGGATTAC
    TCGTTCCCTGGGCACTCACCTTAGATGGACTTTGGCCCCGGCAATAAGATGGTCCTAATG

    LysGlyProValTyrHisArgAlaProLeuGluPhePheGlnGluAlaSerMetCysGlu
663 AAAGGACCCGTCTATCATAGAGCTCCATTGGAGTTCTTTCAGGAAGCCTCTATGTGTGAG
    TTTCCTGGGCAGATAGTATCTCGAGGTAACCTCAAGAAAGTCCTTCGGAGATACACACTC
                       ^
    682 sacl,

    ThrThrArgArgIleGlyArgValThrGlySerAspGlyLysLeuTyrHisIleTyrVal
723 ACAACTAGAAGGATTGGGAGAGTAACTGGTAGTGATGGTAAATTGTACCACATTTATGTG
    TGTTGATCTTCCTAACCCTCTCATTGACCATCACTACCATTTAACATGGTGTAAATACAC

    CysIleAspGlyCysIleIleValLysSerAlaThrLysTyrHisGlnLysValLeuLys
783 TGCATAGATGGATGCATAATAGTTAAGAGCGCCACAAAATATCATCAAAAGGTACTCAAA
    ACGTATCTACCTACGTATTATCAATTCTCGCGGTGTTTTATAGTAGTTTTCCATGAGTTT
               ^
    794 ava3,

    TrpValHisAsnLysLeuAsnCysProLeuTrpValSerSerCysSerAspThrLysAla
843 TGGGTCCACAACAAACTAAATTGCCCTCTATGGGTTTCAAGCTGCTCCGACACAAAAGCA
    ACCCAGGTGTTGTTTGATTTAACGGGAGATACCCAAAGTTCGACGAGGCTGTGTTTTCGT

    GluGlyAlaThrArgLysLysGlnGlnLysProAspArgLeuGluLysGlyArgMetLys
903 GAAGGGGCGACAAGAAAGAAGCAACAAAAACCAGATAGGCTGGAAAAGGGGAGGATGAAG
    CTTCCCCGCTGTTCTTTCTTCGTTGTTTTTGGTCTATCCGACCTTTTCCCCTCCTACTTC

    IleThrProLysGluSerGluLysaspSerLysThrLysProProAspAlaThrIleVal
963 ATAACTCCTAAAGAGTCGGAGAAAGATAGTAAGACCAAACCGCCAGATGCTACGATAGTG
    TATTGAGGATTTCTCAGCCTCTTTCTATCATTCTGGTTTGGCGGTCTACGATGCTATCAC

     ValAspGlyValLysTyrGlnValLysLysLysGlyLysIleLysSerLysAsnThrGln
1023 GTAGATGGTGTCAAATATCAGGTAAAGAAAAAAGGGAAAATCAAGAGTAAGAATACCCAG
     CATCTACCACAGTTTATAGTCCATTTCTTTTTTCCCTTTTAGTTCTCATTCTTATGGGTC

     AspGlyLeuTyrHisAsnLysAsnLysProGlnGluSerArgLysLysLeuGluLysAla
1083 GACGGTTTGTACCACAACAAAAATAAACCTCAAGAGTCACGCAAGAAACTAGAGAAAGCC
     CTGCCAAACATGGTGTTGTTTTTATTTGGAGTTCTCAGTGCGTTCTTTGATCTCTTTCGG
                                                             ^
     1140 bgll,

     LeuLeuAlaTrpAlaValIleAlaLeuValLeuPheGlnValAlaValGlyGluAsnIle
1143 CTGTTGGCATGGGCAGTAATAGCCTTGGTTTTGTTTCAAGTCGCAGTGGGAGAGAACATA
     GACAACCGTACCCGTCATTATCGGAACCAAAACAAAGTTCAGCGTCACCCTCTCTTGTAT
```

FIG.2C

```
     ThrGlnTrpAsnLeuGlnAspAsnGlyThrGluGlyIleGlnArgAlaMetPheGlnArg
1203 ACACAATGGAACTTACAAGACAATGGGACGGAAGGAATACAACGGGCCATGTTCCAAAGA
     TGTGTTACCTTGAATGTTCTGTTACCCTGCCTTCCTTATGTTGCCCGGTACAAGGTTTCT

     GlyValAsnArgSerLeuHisGlyIleTrpProGluLysIleCysThrGlyValProSer
1263 GGCGTAAATAGAAGTCTGCATGGGATCTGGCCAGAGAAAATCTGTACAGGTGTCCCCTCC
     CCGCATTTATCTTCAGACGTACCCTAGACCGGTCTCTTTTAGACATGTCCACATTTTAGG
                                 ^
     1290 ball,

     HisLeuAlaThrAspThrGluLeuLysAlaIleHisGlyMetMetAspAlaSerGluLys
1323 CACTTGGCCACTGATACAGAACTGAAGGCAATTCATGGTATGATGGATGCTAGCGAGAAG
     GTGAACCGGTGACTATGTCTTGACTTCCGTTAAGTACCATACTACCTACGATCGCTCTTC
         ^     ^                                    ^
     1327 ball, 1333 tthIIIl, 1371 nhel,

     ThrAsnTyrThrCysCysArgLeuGlnArgHisGluTrpAsnLysHisGlyTrpCysAsn
1383 ACAAATTACACATGCTGCAGGCTCCAACGCCATGAGTGGAACAAGCATGGTTGGTGCAAT
     TGTTTAATGTGTACGACGTCCGAGGTTGCGGTACTCACCTTGTTCGTACCAACCACGTTA
                   ^
     1397 pstl,

     TrpTyrAsnIleGluProTrpIleValLeuMetAsnLysThrGlnAlaAsnLeuAlaGlu
1443 TGGTACAATATTGAACCTTGGATTGTTCTCATGAATAAAACCCAAGCCAACCTTGCTGAG
     ACCATGTTATAACTTGGAACCTAACAAGAGTACTTATTTTGGGTTCGGTTGGAACGACTC
           ^
     1449 sspl,

     GlyGlnProProArgGluCysAlaValThrCysArgTyrAspArgAspSerAspLeuAsn
1503 GGTCAGCCACCAAGGGAGTGTGCCGTTACATGCCGGTATGACCGAGATAGTGACCTAAAT
     CCAGTCGGTGGTTCCCTCACACGGCAATGTACGGCCATACTGGCTCTATCACTGGATTTA

     ValValThrGlnAlaArgAsnSerProThrProLeuThrGlyCysLysLysGlyLysAsn
1563 GTAGTAACACAAGCTAGGAACAGCCCCACACCATTGACAGGCTGCAAGAAAGGCAAGAAC
     CATCATTGTGTTCGATCCTTGTCGGGGTGTGGTAACTGTCCGACGTTCTTTCCGTTCTTG

     PheSerPheAlaGlyValLeuValGlnGlyProCysAsnPheGluIleAlaValSerAsp
1623 TTCTCCTTTGCAGGTGTGTTGGTACAAGGGCCTTGCAACTTTGAAATAGCTGTAAGTGAT
     AAGAGGAAACGTCCACACAACCATGTTCCCGGAACGTTGAAACTTTATCGACATTCACTA

     ValLeuPheArgGluHisAspCysThrSerValIleGlnGlyThrAlaHisTyrLeuVal
1683 GTGCTGTTTAGAGAGCACGATTGCACAAGTGTGATTCAAGGCACGGCTCACTATCTGGTA
     CACGACAAATCTCTCGTGCTAACGTGTTCACACTAAGTTCCGTGCCGAGTGATAGACCAT

     AspGlyMetThrAsnSerLeuGluSerAlaArgGlnGlyThrAlaLysLeuThrThrTrp
1743 GACGGGATGACCAATTCTCTAGAAAGTGCCAGGCAAGGGACCGCAAAGTTAACTACTTGG
     CTGCCCTACTGGTTAAGAGATCTTTCACGGTCCGTTCCCTGGCGTTTCAATTGATGAACC
                      ^                             ^
     1760 xbal, 1790 hpal,

     LeuGlyArgGlnLeuLysLysLeuGlyLysLysLeuGluAsnLysSerLysThrTrpPhe
1803 TTGGGTAGGCAGCTTAAGAAACTAGGGAAGAAACTGGAAAACAAGAGTAAGACATGGTTT
     AACCCATCCGTCGAATTCTTTGATCCCTTCTTTGACCTTTTGTTCTCATTCTGTACCAAA
                 ^
     1815 afl11,
```

FIG.2D

```
     GlyAlaTyrAlaAlaSerProTyrCysGluValGluArgArgLeuGlyTyrIleTrpTyr
1863 GGGGCATATGCAGCCTCTCCCTACTGCGAGGTAGAACGGAGGCTTGGTTACATCTGGTAT
     CCCCGTATACGTCGGAGAGGGATGACGCTCCATCTTGCCTCCGAACCAATGTAGACCATA
         ^
     1867 ndeI,

     ThrLysAsnCysThrProAlaCysLeuProLysAsnThrLysIleValGlyProGlyArg
1923 ACAAAGAATTGCACCCCTGCCTGTTTACCAAAAAATACAAAGATCGTTGGCCCCGGTAGG
     TGTTTCTTAACGTGGGGACGGACAAATGGTTTTTTATGTTTCTAGCAACCGGGGCCATCC

     PheAspThrAsnAlaGluAspGlyLysIleLeuHisGluMetGlyGlyHisLeuSerGlu
1983 TTCGACACCAATGCGGAGGATGGTAAAATACTGCATGAGATGGGGGGCCACTTGTCAGAG
     AAGCTGTGGTTACGCCTCCTACCATTTTATGACGTACTCTACCCCCCGGTGAACAGTCTC

     ValLeuLeuLeuSerValValValLeuSerAspPheAlaProGluThrAlaSerValVal
2043 GTGCTACTACTCTCAGTGGTAGTGCTTTCCGATTTCGCTCCAGAGACAGCCAGTGTGGTA
     CACGATGATGAGAGTCACCATCACGAAAGGCTAAAGCGAGGTCTCTGTCGGTCACACCAT

     TyrLeuIleLeuHisPheSerIleProGlnGlyHisThrAspIleHisAspCysAspLys
2103 TATTTAATTCTACATTTCTCCATCCCACAAGGACACACTGACATACATGACTGTGATAAA
     ATAAATTAAGATGTAAAGAGGTAGGGTGTTCCTGTGTGACTGTATGTACTGACACTATTT

     AsnGlnLeuAsnLeuThrValGlyLeuThrThrAlaGluValIleProGlySerValTrp
2163 AACCAACTAAACCTCACCGTAGGACTCACAACAGCTGAAGTAATACCTGGGTCAGTTTGG
     TTGGTTGATTTGGAGTGGCATCCTGAGTGTTGTCGACTTCATTATGGACCCAGTCAAACC
                                    ^              ^
     2194 pvuII, 2209 tthIII1,

     AsnLeuGlyLysTyrValCysIleArgProAspTrpTrpProTyrGluThrAlaThrPhe
2223 AATTTGGGCAAATATGTTTGTATAAGACCAGATTGGTGGCCTTATGAGACAGCCACGTTC
     TTAAACCCGTTTATACAAACATATTCTGGTCTAACCACCGGAATACTCTGTCGGTGCAAG
                                ^
     2250 bstXI,

     LeuValPheGluGluValGlyGlnValIleArgIleValLeuArgAlaLeuArgAspLeu
2283 CTAGTGTTTGAAGAGGTGGGTCAAGTGATCAGGATAGTCTTGAGGGCTTTAAGAGATCTA
     GATCACAAACTTCTCCACCCAGTTCACTAGTCCTATCAGAACTCCCGAAATTCTCTAGAT
                              ^                           ^
     2308 bclI, 2336 bglII,

     ThrArgIleTrpThrAlaAlaThrThrThrAlaPheLeuValCysLeuValLysValVal
2343 ACGCGCATTTGGACCGCTGCTACGACTACTGCATTCCTGGTATGTCTGGTGAAGGTGGTG
     TGCGCGTAAACCTGGCGACGATGCTGATGACGTAAGGACCATACAGACCACTTCCACCAC

     ArgGlyGlnValLeuGlnGlyIleLeuTrpLeuIleLeuIleThrGlyAlaGlnGlyLeu
2403 AGAGGCCAAGTGTTGCAAGGCATACTGTGGTTGATACTCATAACAGGGGCACAAGGGCTC
     TCTCCGGTTCACAACGTTCCGTATGACACCAACTATGAGTATTGTCCCCGTGTTCCCGAG

     ProValCysLysProGlyPheTyrTyrAlaIleAlaLysAsnAsnGluIleGlyProLeu
2463 CCAGTTTGCAAACCCGGCTTTTACTACGCCATAGCCAAAAATAATGAGATCGGCCCTCTT
     GGTCAAACGTTTGGGCCGAAAATGATGCGGTATCGGTTTTTATTACTCTAGCCGGGAGAA

     GlyAlaThrGlyLeuThrThrGlnTrpTyrGluTyrSerAspGlyMetArgLeuGlnAsp
2523 GGGGCTACGGGCCTCACCACTCAGTGGTATGAATACTCGGATGGGATGCGGCTGCAGGAC
     CCCCGATGCCCGGAGTGGTGAGTCACCATACTTATGAGCCTACCCTACGCCGACGTCCTG
                                                        ^
     2574 pstI,
```

FIG.2E

```
     ThrGlyValValValTrpCysLysGlyGlyGluIleLysTyrLeuIleTyrCysGluArg
2583 ACGGGAGTTGTAGTGTGGTGTAAAGGTGGAGAGATCAAATATCTAATTACATGTGAGAGG
     TGCCCTCAACATCACACCACATTTCCACCTCTCTAGTTTATAGATTAATGTACACTCTCC

     GluAlaArgTyrLeuAlaIleLeuHisThrArgAlaLeuProThrSerValValPheGlu
2643 GAAGCCAGGTATCTGGCCATTCTACACACGAGAGCCCTGCCGACGTCTGTAGTATTTGAA
     CTTCGGTCCATAGACCGGTAAGATGTGTGCTCTCGGGACGGCTGCAGACATCATAAACTT
         ^        ^                           ^

     2647 bstXI, 2656 ball, 2684 aatII,

     LysIleIleAspGlyLysGluGlnGluAspValValGluMetAspAspAsnPheGluLeu
2703 AAAATCATAGATGGAAAAGAACAAGAGGACGTAGTGGAAATGGATGATAACTTTGAACTC
     TTTTAGTATCTACCTTTTCTTGTTCTCCTGCATCACCTTTACCTACTATTGAAACTTGAG

     GlyLeuCysProCysAspAlaLysProLeuValArgGlyLysPheAsnThrThrLeuLeu
2763 GGTCTTTGCCCGTGTGATGCTAAACCCTTGGTAAGGGGAAAATTTAATACAACACTTCTG
     CCAGAAACGGGCACACTACGATTTGGGAACCATTCCCCTTTTAAATTATGTTGTGAAGAC

     AsnGlyProAlaPheGlnMetValCysProIleGlyTrpThrGlyThrValSerLeuCys
2823 AATGGGCCAGCCTTCCAGATGGTTTGCCCTATAGGATGGACAGGAACTGTGAGTCTGTGT
     TTACCCGGTCGGAAGGTCTACCAAACGGGATATCCTACCTGTCCTTGACACTCAGACACA

     HisTrpSerAsnLysAspThrLeuAlaMetThrValValArgThrTyrLysArgHisArg
2883 CACTGGTCCAATAAGGATACGTTAGCCATGACCGTTGTACGAACATACAAGAGGCACAGG
     GTGACCAGGTTATTCCTATGCAATCGGTACTGGCAACATGCTTGTATGTTCTCCGTGTCC
                                                              ^

     2940 stul,

     ProPheProPheArgGlnGlyCysIleThrGlnLysValIleGlyGlyAspLeuTyrAsp
2943 CCTTTCCCCTTTAGGCAAGGCTGCATTACCCAGAAAGTCATCGGGGGAGACCTCTACGAC
     GGAAAGGGGAAATCCGTTCCGACGTAATGGGTCTTTCAGTAGCCCCCTCTGGAGATGCTG

3003 TGTGCCTTGGGAGGGAACTGGACTTGTGTACCGGGGGACATACTACGATATGTAGATGGG
     ACACGGAACCCTCCCTTGACCTGAACACATGGCCCCCTGTATGATGCTATACATCTACCC

     ProValGluSerCysLysTrpCysGlyTyrLysPheHisLysSerGluGlyLeuProHis
3063 CCTGTCGAGTCTTGCAAGTGGTGTGGTTACAAGTTTCATAAAAGTGAGGGTCTGCCACAC
     GGACAGCTCAGAACGTTCACCACACCAATGTTCAAAGTATTTTCACTCCCAGACGGTGTG

     PheProIleGlyLysCysLysLeuLysAsnGluSerGlyTyrArgGlnValAspGluThr
3123 TTCCCAATTGGCAAGTGCAAGCTGAAGAATGAAAGTGGCTACAGACAAGTAGATGAGACC
     AAGGGTTAACCGTTCACGTTCGACTTCTTACTTTCACCGATGTCTGTTCATCTACTCTGG

     SerCysAsnArgAspGlyValAlaIleValProThrGlySerValLysCysLysIleGly
3183 TCTTGCAACAGAGACGGTGTGGCTATAGTACCAACTGGTTCGGTGAAATGCAAGATAGGG
     AGAACGTTGTCTCTGCCACACCGATATCATGGTTGACCAAGCCACTTTACGTTCTATCCC

     AspThrValValGlnValIleAlaMetAspAspLysLeuGlyProMetProCysArgPro
3243 GACACAGTGGTGCAAGTCATAGCAATGGATGATAAGCTAGGGCCTATGCCTTGCAGACCA
     CTGTGTCACCACGTTCAGTATCGTTACCTACTATTCGATCCCGGATACGGAACGTCTGGT
                                                               ^

     3301 ndel,

     TyrGluIleIleProSerGluGlyProValGluLysThrAlaCysThrPheAsnTyrThr
3303 TATGAAATCATTCCCAGTGAGGGGCCGGTAGAAAAGACGGCATGTACCTTCAACTACACA
     ATACTTTAGTAAGGGTCACTCCCCGGCCATCTTTTCTGCCGTACATGGAAGTTGATGTGT
        ^

     3306 xmnl,
```

FIG.2F

```
     LysThrLeuLysAsnLysTyrTyrGluProArgAspAsnTyrPheGlnGlnTyrMetLeu
3363 AAAACATTAAAGAACAAGTATTATGAGCCTAGGGATAATTATTTCCAACAATACATGTTA
     TTTTGTAATTTCTTGTTCATAATACTCGGATCCCTATTAATAAAGGTTGTTATGTACAAT
                               ^
     3390 avr2,

     LysGlyGluTyrGlnTyrTrpPheAspLeuGluIleThrAspHisHisArgAspTyrPhe
3423 AAAGGGGAGTACCAATATTGGTTTGACCTAGAGATCACTGACCACCACCGGGATTACTTC
     TTTCCCCTCATGGTTATAACCAAACTGGATCTCTAGTGACTGGTGGTGGCCCTAATGAAG
                  ^
     3436 sspl,

     AlaGluSerLeuLeuValIleValValAlaLeuLeuGlyGlyArgTyrValLeuTrpLeu
3483 GCTGAGTCCCTACTGGTGATAGTGGTTGCACTCCTGGGCGGTAGGTACGTGCTCTGGTTA
     CGACTCAGGGATGACCACTATCACCAACGTGAGGACCCGCCATCCATGCACGAGACCAAT

     LeuValThrTyrMetIleLeuSerGluGlnMetThrSerGlyArgProValTrpAlaGly
3543 CTGGTTACATATATGATCCTATCAGAACAAATGACCTCGGGACGTCCAGTATGGGCAGGT
     GACCAATGTATATACTAGGATAGTCTTGTTTACTGGAGCCCTGCAGGTCATACCCGTCCA
                                               ^
     3583 aatII,

     GluIleValMetMetGlyAsnLeuLeuThrHisAspSerIleGluValValThrTyrPhe
3603 GAAATAGTGATGATGGGCAACCTGCTAACACATGACAGTATTGAAGTGGTGACTTATTTC
     CTTTATCACTACTACCCGTTGGACGATTGTGTACTGTCATAACTTCACCACTGAATAAAG

     LeuLeuLeuTyrLeuLeuLeuArgGluGluAsnIleLysLysTrpValIleLeuIleTyr
3663 TTACTACTATACCTACTACTAAGAGAGGAAAACATCAAAAAATGGGTTATACTTATATAC
     AATGATGATATGGATGATGATTCTCTCCTTTTGTAGTTTTTTACCCAATATGAATATATG

     HisIleIleValMetHisProLeuLysSerValThrValIleLeuLeuMetValGlyGly
3723 CACATCATAGTAATGCACCCACTAAAATCAGTGACGGTGATACTGCTAATGGTTGGAGGG
     GTGTAGTATCATTACGTGGGTGATTTTAGTCACTGCCACTATGACGATTACCAACCTCCC

     MetAlaArgAlaGluProGlyAlaGlnSerPheLeuGluGlnValAspLeuSerPheSer
3783 ATGGCAAGGGCAGAACCAGGCGCCCAGAGCTTCCTAGAGCAGGTGGACCTGAGTTTTTCA
     TACCGTTCCCGTCTTGGTCCGCGGGTCTCGAAGGATCTCGTCCACCTGAACTCAAAAAGT
                       ^
     3801 narl,

     MetIleThrLeuIleValValGlyLeuValIleAlaArgArgAspProThrValValPro
3843 ATGATCACGCTCATTGTAGTAGGTCTGGTCATTGCCAGGCGCGACCCCACTGTGGTGCCA
     TACTAGTGCGAGTAACATCATCCAGACCAGTAACGGTCCGCGCTGGGGTGACACCACGGT
      ^                                                          ^
     3844 bcll, 3902 spel,

     LeuValThrIleValAlaAlaLeuArgValThrGlyLeuGlyPheGlyProGlyValAsp
3903 CTAGTCACAATAGTTGCAGCACTGAGGGTAACGGGACTAGGCTTTGGGCCCGGAGTGGAT
     GATCAGTGTTATCAACGTCGTGACTCCCATTGCCCTGATCCGAAACCCGGGCCTCACCTA
                                                  ^
     3948 apal,

     ValAlaMetAlaValLeuThrLeuThrLeuLeuMetIleSerTyrValThrAspTyrPhe
3963 GTAGCTATGGCAGTCCTAACCTTGACCCTACTGATGATTAGTTATGTGACAGACTACTTC
     CATCGATACCGTCAGGATTGGAACTGGGATGACTACTAATCAATACACTGTCTGATGAAG

     ArgTyrLysArgTrpLeuGlnCysIleLeuSerLeuIleAlaGlyValPheLeuIleArg
4023 AGGTACAAAAGGTGGCTACAATGTATCCTCAGCTTAATAGCCGGGGTTTTCCTTATACGA
     TCCATGTTTTCCACCGATGTTACATAGGAGTCGAATTATCGGCCCCAAAAGGAATATGCT
```

FIG.2G

```
     SerLeuLysHisLeuGlyGluIleGluThrProGluLeuThrIleProAsnTrpArgPro
4083 AGCCTTAAACATCTGGGCGAGATTGAGACCCCTGAGCTGACCATACCGAACTGGAGGCCA
     TCGGAATTTGTAGACCCGCTCTAACTCTGGGGACTCGACTGGTATGGCTTGACCTCCGGT

     LeuThrPheIleLeuLeuTyrLeuThrSerAlaThrValValThrArgTrpLysValAsp
4143 CTAACCTTCATACTATTGTACCTGACTTCAGCAACAGTTGTCACACGATGGAAAGTTGAC
     GATTGGAAGTATGATAACATGGACTGAAGTCGTTGTCAACAGTGTGCTACCTTTCAACTG

     IleAlaGlyIleLeuLeuGlnGlyProGlnSerPheCysOP
4203 ATAGCTGGCATATTACTGCAAGGGCCCCAATCCTTCTGCTGATTGCCACCTATGGGCT
     TATCGACCGTATAATGACGTTCCCGGGGTTAGGAAGACGACTAACGGTGGATACCCGA
                         ^
     4224 apal,

4261 GACTTCCTGACCCTTGTATTGATCCTGCCCACCCACGAATTAGTCAAGTTGTACTACCTG
     CTGAAGGACTGGGAACATAACTAGGACGGGTGGGTGCTTAATCAGTTCAACATGATGGAC

4321 AAGACCGTCAAGACTGATGTGGAAAAGAGTTGGCTAGGGGGGGTGGACTACAAGACAATT
     TTCTGGCAGTTCTGACTACACCTTTTCTCAACCGATCCCCCCCACCTGATGTTCTGTTAA

                      MetAspGluSerGlyGluGlyValTyrLeuPheProSerLysGln
4381 GGCTCTATTTATGATATGGATGAAAGTGGAGAGGGCGTGTACCTTTTCCCATCCAAACAG
     CCGAGATAAATACTATACCTACTTTCACCTCTCCCGCACATGGAAAAGGGTAGGTTTGTC

     AsnGlyLysLysAsnValSerIleLeuLeuProLeuIleArgAlaThrLeuIleSerCys
4441 AATGGCAAGAAAAATGTCAGCATACTCTTGCCCCTCATTAGAGCTACACTAATAAGCTGT
     TTACCGTTCTTTTTACAGTCGTATGAGAACGGGGAGTAATCTCGATGTGATTATTCGACA
                                                             ^
     4497 tthIII1,

     IleSerSerLysTrpGlnMetValTyrMetAlaTyrLeuThrLeuAspPheMetTyrTyr
4501 ATCAGCAGCAAATGGCAGATGGTGTACATGGCTTACCTAACCTTGGACTTTATGTACTAC
     TAGTCGTCGTTTACCGTCTACCACATGTACCGAATGGATTGGAACCTGAAATACATGATG

     IleHisArgLysValIleGluGluIleSerGlyGlyThrAsnValIleSerArgValIle
4561 ATACACAGAAAGGTTATAGAAGAGATCTCAGGGGGCACCAATGTGATATCTAGGGTGATA
     TATGTGTCTTTCCAATATCTTCTCTAGAGTCCCCCGTGGTTACACTATAGATCCCACTAT
                           ^                     ^
     4583 bgl11, 4605 ecor5,

     AlaAlaLeuIleGluLeuAsnTrpSerMetGluGluGluGluSerLysGlyLeuLysLys
4621 GCAGCACTCATAGAGCTAAACTGGTCTATGGAAGAAGAAGAAAGCAAGGGCTTAAAGAAG
     CGTCGTGAGTATCTCGATTTGACCAGATACCTTCTTCTTCTTTCGTTCCCGAATTTCTTC

     PhePheIleLeuSerGlyArgLeuLysAlaLeuIleIleLysHisLysValArgAsnGln
4681 TTTTTTATACTATCTGGGAGGTTGAAGGCCCTTATAATAAAGCATAAGGTTAGGAACCAG
     AAAAAATATGATAGACCCTCCAACTTCCGGGAATATTATTTCGTATTCCAATCCTTGGTC

     ThrValAlaSerTrpTyrGlyGluGluGluValTyrGlyMetProLysValValThrIle
4741 ACCGTAGCAAGCTGGTATGGGGAGGAAGAAGTCTACGGCATGCCAAAAGTAGTGACCATA
     TGGCATCGTTCGACCATACCCCTCCTTCTTCAGATGCCGTACGGTTTTCATCACTGGTAT
                                         ^
     4778 sphl,

     IleArgAlaCysSerLeuAsnLysAsnLysHisCysIleIleCysThrValCysGluAla
4801 ATAAGGGCTTGCTCACTAAACAAGAACAAGCATTGCATAATATGCACAGTATGTGAGGCT
     TATTCCCGAACGAGTGATTTGTTCTTGTTCGTAACGTATTATACGTGTCATACACTCCGA
```

FIG.2H

```
     LysLysTrpLysGlyGlyAsnCysProLysCysGlyArgHisGlyLysProIleThrCys
4861 AAGAAGTGGAAGGGTGGCAACTGCCCTAAATGCGGCCGCCACGGGAAGCCCATCACTTGT
     TTCTTCACCTTCCCACCGTTGACGGGATTTACGCCGGCGGTGCCCTTCGGGTAGTGAACA
                                     ^
     4893 xma3,

     GlyMetThrLeuAlaAspPheGluGluArgHisTyrLysArgIlePheIleArgGluGly
4921 GGGATGACTCTAGCGGATTTTGAAGAGAGGCACTACAAGAGAATTTTCATAAGAGAGGGT
     CCCTACTGAGATCGCCTAAAACTTCTCTCCGTGATGTTCTCTTAAAAGTATTCTCTCCCA

     ThrPheGluGlyProPheArgGlnGluHisSerGlyPheValGlnTyrThrAlaArgGly
4981 ACATTCGAAGGACCCTTCAGGCAGGAACATAGCGGGTTTGTACAATACACCGCTAGGGGA
     TGTAAGCTTCCTGGGAAGTCCGTCCTTGTATCGCCCAAACATGTTATGTGGCGATCCCCT

     GlnLeuPheLeuArgAsnLeuProIleLeuAlaThrLysValLysMetLeuMetValGly
5041 CAATTGTTCCTGAGGAATTTACCCATATTGGCAACCAAAGTAAAAATGCTTATGGTAGGC
     GTTAACAAGGACTCCTTAAATGGGTATAACCGTTGGTTTCATTTTTACGAATACCATCCG
             ^
     5049 mstII,

     AsnLeuGlyValGluIleGlyAspLeuGluHisLeuGlyTrpIleLeuLysMetGlnIle
5101 AACCTAGGGGTAGAAATCGGTGATCTAGAACACCTAGGATGGATCTTAAAAATGCAGATC
     TTGGATCCCCATCTTTAGCCACTAGATCTTGTGGATCCTACCTAGAATTTTTACGTCTAG
       ^                    ^        ^                      ^
     5103 avr2, 5124 xbal, 5133 avr2, 5156 bglll,

     PheValLysThrLeuThrGlyLysThrIleThrLeuGluValGluProSerAspThrIle
5161 TTCGTGAAAACCCTGACCGGCAAGACCATCACCCTGGAGGTGGAGCCCAGTGACACCATC
     AAGCACTTTTGGGACTGGCCGTTCTGGTAGTGGGACCTCCACCTCGGGTCACTGTGGTAG
                              ^
     5186 bstXI,

     GluAsnValLysAlaLysIleGlnAspLysGluGlyIleProProAspGlnGlnArgLeu
5221 GAGAACGTGAAGGCCAAGATCCAGGATAAGGAAGGCATTCCCCCTGACCAGCAGAGGCTC
     CTCTTGCACTTCCGGTTCTAGGTCCTATTCCTTCCGTAAGGGGGACTGGTCGTCTCCGAG
                                  ^
     5251 xmnl,

     IlePheAlaGlyLysGlnLeuGluAspGlyArgSerLeuSerAspTyrAsnIleGlnLys
5281 ATCTTTGCCGGCAAGCAGCTGGAAGATGGCCGCTCTCTTTCTGATTACAACATCCAGAAA
     TAGAAACGGCCGTTCGTCGACCTTCTACCGGCGAGAGAAAGACTAATGTTGTAGGTCTTT
           ^        ^
     5287 nael, 5296 pvull,

     GluSerThrLeuHisLeuValLeuArgLeuArgGlySerGlyProAlaValCysLysLys
5341 GAGTCGACCCTGCACCTGGTCCTCCGTCTGAGGGGTAGTGGGCCTGCCGTGTGCAAAAAG
     CTCAGCTGGGACGTGGACCAGGAGGCAGACTCCCCATCACCCGGACGGCACACGTTTTTC
       ^
     5343 sall,

     IleThrGluHisGluLysCysHisValAsnIleLeuAspLysLeuThrAlaPhePheGly
5401 ATTACTGAGCATGAGAAATGCCATGTCAACATACTAGACAAATTGACCGCATTTTTCGGG
     TAATGACTCGTACTCTTTACGGTACAGTTGTATGATCTGTTTAACTGGCGTAAAAAGCCC

     ValMetProArgGlyThrThrProArgAlaProValLysIleProThrAlaLeuLeuLys
5461 GTTATGCCAAGAGGTACCACACCAAGGGCTCCGGTGAAGATTCCAACCGCATTGCTAAAA
     CAATACGGTTCTCCATGGTGTGGTTCCCGAGGCCACTTCTAAGGTTGGCGTAACGATTTT
                 ^
     5473 kpnl,
```

FIG.2I

```
     ValArgArgGlyLeuGluThrGlyTrpAlaTyrThrHisGlnGlyGlyIleSerSerVal
5521 GTGAGGAGGGGACTGGAAACCGGATGGGCCTACACACACCAAGGCGGCATAAGCTCAGTA
     CACTCCTCCCCTGACCTTTGGCCTACCCGGATGTGTGTGGTTCCGCCGTATTCGAGTCAT

     AspHisValThrAlaGlyLysAspLeuLeuValCysAspSerMetGlyArgThrArgVal
5581 GACCATGTGACCGCAGGCAAAGACCTACTGGTTTGTGATAGTATGGGTAGGACAAGAGTG
     CTGGTACACTGGCGTCCGTTTCTGGATGACCAAACACTATCATACCCATCCTGTTCTCAC

     ValCysGlnSerAsnAsnLysLeuThrAspGluThrGluTyrGlyValLysThrAspSer
5641 GTTTGCCAAAGTAACAACAAGTTAACTGATGAGACAGAATATGGTGTCAAGACGGACTCC
     CAAACGGTTTCATTGTTGTTCAATTGACTACTCTGTCTTATACCACAGTTCTGCCTGAGG
                         ^
     5661 hpal,

     GlyCysProAspGlyAlaArgCysTyrValLeuAsnProGluAlaValAsnIleSerGly
5701 GGATGTCCAGATGGTGCCAGGTGCTACGTATTAAATCCAGAGGCAGTAAATATATCAGGG
     CCTACAGGTCTACCACGGTCCACGATGCATAATTTAGGTCTCCGTCATTTATATAGTCCC

     SerLysGlyAlaAlaValHisLeuGlnLysThrGlyGlyGluPheThrCysValThrAla
5761 TCCAAGGGAGCTGCTGTACACCTCCAAAAAACAGGTGGGGAATTCACATGTGTTACTGCA
     AGGTTCCCTCGACGACATGTGGAGGTTTTTTGTCCACCCCTTAAGTGTACACAATGACGT
                                            ^
     5800 ecorl,

     SerGlyThrProAlaPhePheAspLeuLysAsnLeuLysGlyTrpSerGlyLeuProIle
5821 TCGGGAACTCCAGCCTTCTTTGACCTGAAAAATTTGAAGGGATGGTCAGGTCTACCCATA
     AGCCCTTGAGGTCGGAAGAAACTGGACTTTTTAAACTTCCCTACCAGTCCAGATGGGTAT

     PheGluAlaSerSerGlyArgValValGlyArgValLysValGlyLysAsnGluGluSer
5881 TTTGAGGCTTCTAGTGGCAGGGTGGTCGGCAGAGTTAAAGTAGGAAAGAATGAGGAATCC
     AAACTCCGAAGATCACCGTCCCACCAGCCGTCTCAATTTCATCCTTTCTTACTCCTTAGG

     LysProThrLysLeuMetSerGlyIleGlnThrValSerLysSerThrAlaAspLeuThr
5941 AAGCCCACAAAATTAATGAGTGGTATCCAAACCGTCTCAAAAAGCACAGCCGATTTAACA
     TTCGGGTGTTTTAATTACTCACCATAGGTTTGGCAGAGTTTTTCGTGTCGGCTAAATTGT

     GluMetValLysLysIleThrSerMetAsnArgGlyAspPheLysGlnIleThrLeuAla
6001 GAGATGGTCAAGAAGATAACCAGCATGAACAGGGGAGACTTTAAGCAGATAACCCTTGCA
     CTCTACCAGTTCTTCTATTGGTCGTACTTGTCCCCTCTGAAATTCGTCTATTGGGAACGT

     ThrGlyAlaGlyLysThrThrGluLeuProLysAlaValIleGluGluIleGlyArgHis
6061 ACAGGGGCAGGAAAAACTACAGAACTCCCAAAGGCAGTGATAGAGGAGATAGGAAGACAC
     TGTCCCCGTCCTTTTTGATGTCTTGAGGGTTTCCGTCACTATCTCCTCTATCCTTCTGTG

     LysArgValLeuValLeuIleProLeuArgAlaAlaAlaGluSerValTyrGlnTyrMet
6121 AAGCGGGTGCTAGTGCTTATACCATTGAGAGCAGCAGCTGAGTCAGTCTATCAATACATG
     TTCGCCCACGATCACGAATATGGTAACTCTCGTCGTCGACTCAGTCAGATAGTTATGTAC
                                       ^  ^
     6155 pvull, 6158 tthIIIl,

     ArgLeuLysHisProSerIleSerPheAsnLeuArgIleGlyAspMetLysGluGlyAsp
6181 AGATTGAAACATCCCAGTATCTCCTTCAACTTAAGAATAGGGGACATGAAAGAAGGGGAC
     TCTAACTTTGTAGGGTCATAGAGGAAGTTGAATTCTTATCCCCTGTACTTTCTTCCCCTG
                                 ^
     6210 aflll,

     MetAlaThrGlyIleThrTyrAlaSerTyrGlyTyrPheCysGlnMetProGlnProLys
6241 ATGGCAACTGGGATCACCTACGCCTCATATGGATATTTTTGCCAAATGCCGCAGCCGAAG
     TACCGTTGACCCTAGTGGATGCGGAGTATACCTATAAAAACGGTTTACGGCGTCGGCTTC
                               ^
     6266 ndel,
```

FIG.2J

```
      LeuArgAlaAlaMetValGluTyrSerTyrIlePheLeuAspGluTyrHisCysAlaThr
6301  CTCAGGGCCGCAATGGTAGAGTATTCATACATATTTCTGGATGAGTATCACTGTGCTACT
      GAGTCCCGGCGTTACCATCTCATAAGTATGTATAAAGACCTACTCATAGTGACACGATGA

      ProGluGlnLeuAlaValIleGlyLysIleHisArgPheSerGluSerIleArgValVal
6361  CCTGAGCAGTTGGCTGTCATAGGAAAAATTCACAGATTTTCTGAAAGCATAAGGGTGGTT
      GGACTCGTCAACCGACAGTATCCTTTTTAAGTGTCTAAAAGACTTTCGTATTCCCACCAA

      AlaMetThrAlaThrProAlaGlySerValThrThrThrGlyGlnLysHisProIleGlu
6421  GCTATGACCGCCACCCCAGCAGGGTCAGTAACTACAACAGGGCAAAAACACCCAATAGAA
      CGATACTGGCGGTGGGGTCGTCCCAGTCATTGATGTTGTCCCGTTTTTGTGGGTTATCTT

      GluPheIleAlaProGluValMetLysGlyGluAspLeuGlySerGlnPheLeuAspIle
6481  GAATTCATAGCTCCTGAGGTGATGAAAGGGGAAGACCTTGGAAGCCAGTTCCTTGACATA
      CTTAAGTATCGAGGACTCCACTACTTTCCCCTTCTGGAACCTTCGGTCAAGGAACTGTAT
          ^                ^
      6481 ecorl, 6493 mstII,

      AlaGlyLeuLysIleProValGluGluMetLysGlyAsnMetLeuValPheValProThr
6541  GCGGGGCTAAAAATCCCGGTTGAGGAGATGAAGGGTAACATGCTGGTCTTCGTACCCACA
      CGCCCCGATTTTTAGGGCCAACTCCTCTACTTCCCATTGTACGACCAGAAGCATGGGTGT

      ArgAsnMetAlaValAspValAlaLysLysLeuLysAlaLysGlyTyrAsnSerGlyTyr
6601  AGAAACATGGCAGTTGATGTAGCCAAGAAACTAAAAGCCAAGGGCTACAACTCAGGGTAT
      TCTTTGTACCGTCAACTACATCGGTTCTTTGATTTTCGGTTCCCGATGTTGAGTCCCATA

      TyrTyrSerGlyGluAspProAlaAsnLeuArgValValThrSerGlnSerProTyrVal
6661  TACTACAGTGGGGAAGACCCGGCTAACTTGAGGGTGGTAACATCACAGTCCCCATACGTC
      ATGATGTCACCCCTTCTGGGCCGATTGAACTCCCACCATTGTAGTGTCAGGGGTATGCAG

      ValValAlaThrAsnAlaIleGluSerGlyValThrLeuProAspLeuAspThrValVal
6721  GTAGTAGCCACCAATGCCATTGAGTCAGGGGTAACGCTGCCAGATTTAGATACAGTTGTT
      CATCATCGGTGGTTACGGTAACTCAGTCCCCATTGCGACGGTCTAAATCTATGTCAACAA

      AspThrGlyLeuLysCysGluLysArgValArgValSerSerLysIleProPheIleVal
6781  GACACAGGTCTGAAGTGTGAAAAGAGGGTGAGGGTGTCATCAAAAATACCTTTCATAGTA
      CTGTGTCCAGACTTCACACTTTTCTCCCACTCCCACAGTAGTTTTTATGGAAAGTATCAT

      ThrGlyLeuLysArgMetAlaValThrValGlyGluGlnAlaGlnArgArgGlyArgVal
6841  ACAGGCCTTAAAAGAATGGCTGTCACTGTGGGCGAACAGGCTCAGCGAAGAGGCAGGGTA
      TGTCCGGAATTTTCTTACCGACAGTGACACCCGCTTGTCCGAGTCGCTTCTCCGTCCCAT
        ^
      6843 stul,

      GlyArgValLysProGlyArgTyrTyrArgSerGlnGluThrAlaThrGlySerLysAsp
6901  GGTAGAGTGAAGCCCGGTAGGTACTATAGAAGCCAGGAAACAGCGACCGGGTCAAAGGAC
      CCATCTCACTTCGGGCCATCCATGATATCTTCGGTCCTTTGTCGCTGGCCCAGTTTCCTG
                                                    ^
      6945 tthIII1,

      TyrHisTyrAspLeuLeuGlnAlaHisArgTyrGlyIleGluAspGlyIleAsnValThr
6961  TACCACTATGACCTGTTACAGGCACACAGGTATGGGATAGAAGATGGAATCAACGTGACA
      ATGGTGATACTGGACAATGTCCGTGTGTCCATACCCTATCTTCTACCTTAGTTGCACTGT
              ^                                                ^
      6973 tthIII1, 7017 tthIII1,

      LysSerPheArgGluMetAsnTyrAspTrpSerLeuTyrGluGluAspSerLeuLeuIle
7021  AAGTCCTTTAGGGAAATGAATTACGATTGGAGCCTGTACGAGGAGGACAGCTTGCTGATA
      TTCAGGAAATCCCTTTACTTAATGCTAACCTCGGACATGCTCCTCCTGTCGAACGACTAT
```

FIG.2K

```
     ThrGlnLeuGluIleLeuAsnAsnLeuLeuIleSerGluAspLeuProAlaAlaValLys
7081 ACCCAGCTGGAGATACTGAACAATCTACTCATCTCTGAAGACCTACCAGCAGCAGTAAAA
     TGGGTCGACCTCTATGACTTGTTAGATGAGTAGAGACTTCTGGATGGTCGTCGTCATTTT
        ^
     7084 pvull,

     AsnIleMetAlaArgThrAspHisProGluProIleGlnLeuAlaTyrAsnSerTyrGlu
7141 AACATCATGGCAAGGACTGATCACCCAGAACCAATCCAGCTTGCATACAACAGTTATGAG
     TTGTAGTACCGTTCCTGACTAGTGGGTCTTGGTTAGGTCGAACGTATGTTGTCAATACTC
                     ^
     7158 bcll,

     ValGlnValProValLeuPheProLysIleArgAsnGlyGluValThrAspThrTyrGlu
7201 GTCCAGGTCCCTGTACTGTTTCCAAAAATAAGGAATGGGGAGGTTACAGATACTTACGAG
     CAGGTCCAGGGACATGACAAAGGTTTTTATTCCTTACCCCTCCAATGTCTATGAATGCTC

     AsnTyrSerPheLeuAsnAlaArgLysLeuGlyGluAspValProValTyrIleTyrAla
7261 AACTACTCATTCCTAAATGCAAGAAAACTAGGGGAAGATGTACCTGTGTACATTTATGCC
     TTGATGAGTAAGGATTTACGTTCTTTTGATCCCCTTCTACATGGACACATGTAAATACGG

     ThrGluAspGluAspLeuAlaValAspLeuLeuGlyLeuAspTrpProAspProGlyAsn
7321 ACCGAAGATGAAGACCTGGCAGTAGACCTTCTAGGCTTGGACTGGCCCGACCCAGGGAAC
     TGGCTTCTACTTCTGGACCGTCATCTGGAAGATCCGAACCTGACCGGGCTGGGTCCCTTG

     GlnGlnValValGluThrGlyLysAlaLeuLysGlnValValGlyLeuSerSerAlaGlu
7381 CAGCAAGTAGTGGAGACTGGGAAAGCACTGAAGCAAGTGGTAGGACTGTCCTCTGCTGAG
     GTCGTTCATCACCTCTGACCCTTTCGTGACTTCGTTCACCATCCTGACAGGAGACGACTC
                                                                ^
     7440 bsml,

     AsnAlaLeuLeuIleAlaLeuPheGlyTyrValGlyTyrGlnAlaLeuSerLysArgHis
7441 AATGCCCTGCTCATAGCCCTGTTTGGGTATGTAGGATATCAAGCTTTGTCAAAAAGACAC
     TTACGGGACGAGTATCGGGACAAACCCATACATCCTATAGTTCGAAACAGTTTTTCTGTG
                                       ^     ^
     7475 ecor5, 7481 hindlll,

     ValProMetIleThrAspIleTyrThrIleGluAspGlnArgLeuGluAspThrThrHis
7501 GTCCCAATGATCACAGACATATACACCATAGAAGATCAAAGACTAGAGGACACAACCCAC
     CAGGGTTACTAGTGTCTGTATATGTGGTATCTTCTAGTTTCTGATCTCCTGTGTTGGGTG
            ^
     7508 bcll,

     LeuGlnTyrAlaProAsnAlaIleArgThrGluGlyLysGluThrGluLeuLysGluLeu
7561 CTCCAATATGCACCTAATGCTATAAGAACTGAGGGGAAGGAGACTGAACTAAAGGAATTA
     GAGGTTATACGTGGATTACGATATTCTTGACTCCCCTTCCTCTGACTTGATTTCCTTAAT

     AlaValGlyAspMetAspArgIleMetGluSerIleSerAspTyrAlaSerGlyGlyLeu
7621 GCAGTGGGTGACATGGACAGAATCATGGAATCCATCTCAGATTATGCATCAGGAGGGTTG
     CGTCACCCACTGTACCTGTCTTAGTACCTTAGGTAGAGTCTAATACGTAGTCCTCCCAAC
                                                ^
     7664 ava3,

     ThrPheIleArgSerGlnAlaGluLysValArgSerAlaProAlaPheLysGluAsnVal
7681 ACATTCATAAGATCTCAGGCAGAGAAAGTAAGATCTGCCCCTGCATTCAAAGAAAACGTG
     TGTAAGTATTCTAGAGTCCGTCTCTTTCATTCTAGACGGGGACGTAAGTTTCTTTTGCAC
              ^                    ^
     7690 bglll, 7711 bglll,
```

FIG.2L

```
     GluAlaAlaLysGlyTyrValGlnLysPheIleAspAlaLeuIleGluAsnLysGluThr
7741 GAAGCTGCAAAAGGGTACGTCCAAAAGTTTATTGATGCTCTTATTGAAAACAAAGAAACC
     CTTCGACGTTTTCCCATGCAGGTTTTCAAATAACTACGAGAATAACTTTTGTTTCTTTGG

     IleIleArgTyrGlyLeuTrpGlyThrHisThrAlaLeuTyrLysSerIleAlaAlaArg
7801 ATAATCAGATATGGCTTATGGGGAACACACACGGCACTTTACAAGAGTATTGCCGCAAGA
     TATTAGTCTATACCGAATACCCCTTGTGTGTGCCGTGAAATGTTCTCATAACGGCGTTCT

     LeuGlyHisGluThrAlaPheAlaThrLeuValIleLysTrpLeuAlaPheGlyGlyGlu
7861 CTGGGGCATGAAACAGCATTTGCTACGCTAGTGATAAAGTGGCTAGCCTTCGGGGGTGAG
     GACCCCGTACTTTGTCGTAAACGATGCGATCACTATTTCACCGATCGGAAGCCCCCACTC
                                              ^
     7902 nheI,

     ProValSerAspHisValArgGlnAlaThrValAspLeuValValTyrTyrValMetAsn
7921 CCGGTGTCAGATCATGTGAGACAGGCGACCGTTGACCTGGTCGTTTATTATGTGATGAAC
     GGCCACAGTCTAGTACACTCTGTCCGCTGGCAACTGGACCAGCAAATAATACACTACTTG
                                      ^
     7954 tthIII1,

     LysProSerPhePRoGlyAspSerGluThrGlnGlnGluGlyArgArgPheValAlaSer
7981 AAACCCTCTTTCCCAGGGGATTCCGAAACCCAGCAGGAGGGGAGGCGATTCGTTGCCAGC
     TTTGGGAGAAAGGGTCCCCTAAGGCTTTGGGTCGTCCTCCCCTCCGCTAAGCAACGGTCG

8041 TTATTCATCTCCGCTCTGGCAACCTACACATACAAGACTTGGAACTACCACAACCTCTCC
     AATAAGTAGAGGCGAGACCGTTGGATGTGTATGTTCTGAACCTTGATGGTGTTGGAGAGG

     LysValValGluProAlaLeuAlaTyrLeuProTyrAlaThrSerAlaLeuLysMetPhe
8101 AAGGTAGTAGAACCAGCTTTGGCATACCTCCCCTACGCTACCAGTGCACTGAAAATGTTC
     TTCCATCATCTTGGTCGAAACCGTATGGAGGGGATGCGATGGTCACGTGACTTTTACAAG
                                                       ^
     8151 xmnI,

     ThrProThrArgLeuGluSerGluValIleLeuSerThrThrIleTyrLysThrTyrLeu
8161 ACCCCAACTAGACTGGAGAGCGAGGTTATACTTAGCACTACAATATACAAAACTTACCTC
     TGGGGTTGATCTGACCTCTCGCTCCAATATGAATCGTGATGTTATATGTTTTGAATGGAG

     SerIleArgLysGlyLysSerAspGlyLeuLeuGlyThrGlyIleSerAlaAlaMetGlu
8221 TCAATAAGGAAGGGGAAAAGTGATGGACTCTTGGGTACAGGGATTAGTGCGGCAATGGAA
     AGTTATTCCTTCCCCTTTTCACTACCTGAGAACCCATGTCCCTAATCACGCCGTTACCTT

     IleLeuSerGlnAsnProValSerValGlyIleSerValMetLeuGlyValGlyAlaIle
8281 ATTCTGTCACAGAACCCGGTATCGGTAGGCATATCTGTTATGCTGGGGGTGGGGGCAATT
     TAAGACAGTGTCTTGGGCCATAGCCATCCGTATAGACAATACGACCCCCACCCCCGTTAA
        ^
     8284 tthIII1,

     AlaAlaHisAsnAlaIleGluSerSerGluGlnLysArgThrLeuLeuMetLysValPhe
8341 GCCGCTCACAATGCCATTGAGTCTAGCGAACAAAAAAGGACCCTGTTGATGAAAGTGTTC
     CGGCGAGTGTTACGGTAACTCAGATCGCTTGTTTTTTCCTGGGACAACTACTTTCACAAG
                                                       ^
     8391 xmnI,

     ValLysAsnPheTrpSerGlnAlaAlaThrAspGluLeuValLysGluAsnProGluLys
8401 GTAAAAAACTTCTGGAGCCAGGCAGCAACAGATGAATTGGTGAAGGAAAATCCAGAAAAA
     CATTTTTTGAAGACCTCGGTCCGTCGTTGTCTACTTAACCACTTCCTTTTAGGTCTTTTT
```

FIG.2M

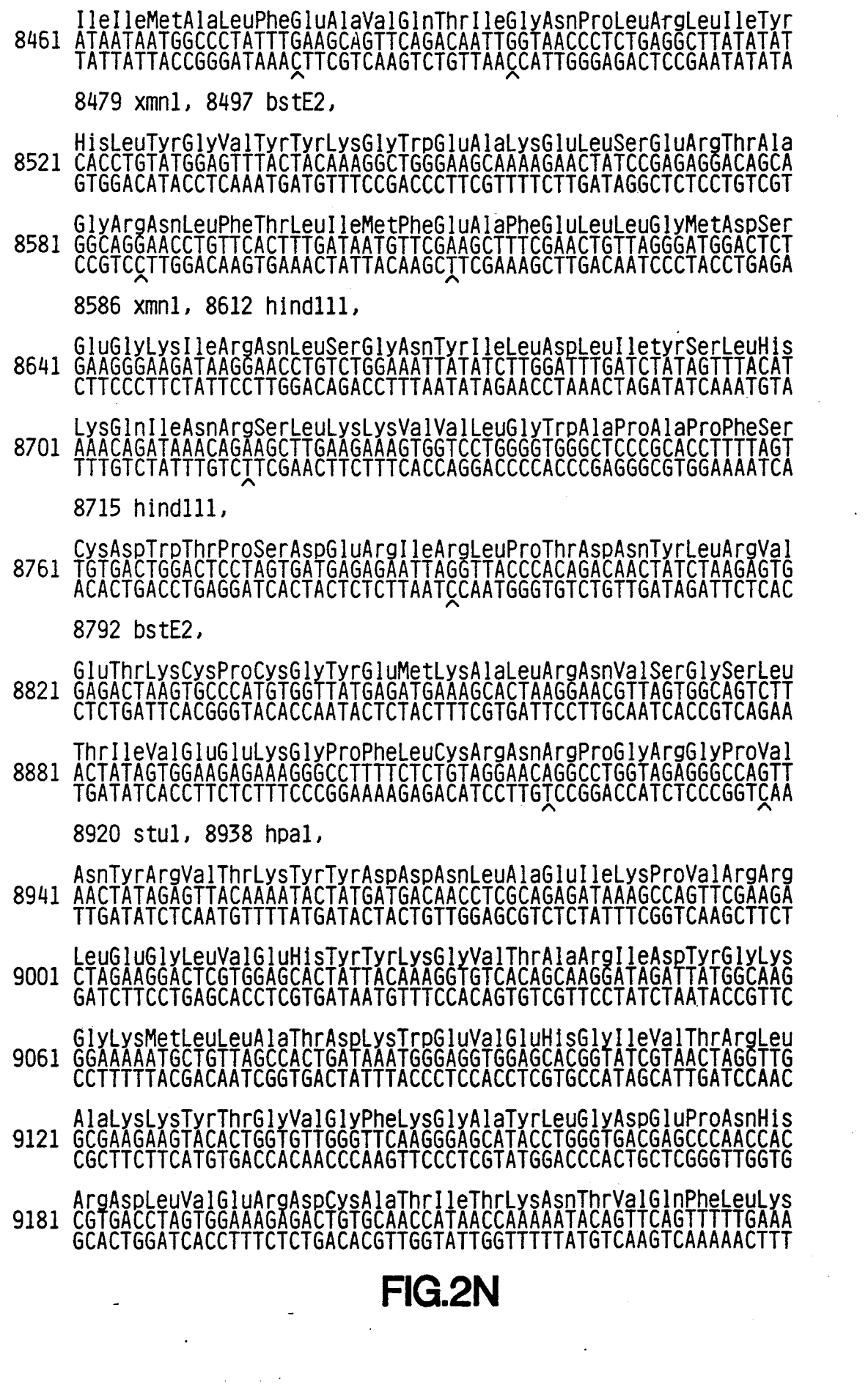

```
     IleIleMetAlaLeuPheGluAlaValGlnThrIleGlyAsnProLeuArgLeuIleTyr
8461 ATAATAATGGCCCTATTTGAAGCAGTTCAGACAATTGGTAACCCTCTGAGGCTTATATAT
     TATTATTACCGGGATAAACTTCGTCAAGTCTGTTAACCATTGGGAGACTCCGAATATATA

     8479 xmn1, 8497 bstE2,

     HisLeuTyrGlyValTyrTyrLysGlyTrpGluAlaLysGluLeuSerGluArgThrAla
8521 CACCTGTATGGAGTTTACTACAAAGGCTGGGAAGCAAAAGAACTATCCGAGAGGACAGCA
     GTGGACATACCTCAAATGATGTTTCCGACCCTTCGTTTTCTTGATAGGCTCTCCTGTCGT

     GlyArgAsnLeuPheThrLeuIleMetPheGluAlaPheGluLeuLeuGlyMetAspSer
8581 GGCAGGAACCTGTTCACTTTGATAATGTTCGAAGCTTTCGAACTGTTAGGGATGGACTCT
     CCGTCCTTGGACAAGTGAAACTATTACAAGCTTCGAAAGCTTGACAATCCCTACCTGAGA

     8586 xmn1, 8612 hind111,

     GluGlyLysIleArgAsnLeuSerGlyAsnTyrIleLeuAspLeuIletyrSerLeuHis
8641 GAAGGGAAGATAAGGAACCTGTCTGGAAATTATATCTTGGATTTGATCTATAGTTTACAT
     CTTCCCTTCTATTCCTTGGACAGACCTTTAATATAGAACCTAAACTAGATATCAAATGTA

     LysGlnIleAsnArgSerLeuLysLysValValLeuGlyTrpAlaProAlaProPheSer
8701 AAACAGATAAACAGAAGCTTGAAGAAAGTGGTCCTGGGGTGGGCTCCCGCACCTTTTAGT
     TTTGTCTATTTGTCTTCGAACTTCTTTCACCAGGACCCCACCCGAGGGCGTGGAAAATCA

     8715 hind111,

     CysAspTrpThrProSerAspGluArgIleArgLeuProThrAspAsnTyrLeuArgVal
8761 TGTGACTGGACTCCTAGTGATGAGAGAATTAGGTTACCCACAGACAACTATCTAAGAGTG
     ACACTGACCTGAGGATCACTACTCTCTTAATCCAATGGGTGTCTGTTGATAGATTCTCAC

     8792 bstE2,

     GluThrLysCysProCysGlyTyrGluMetLysAlaLeuArgAsnValSerGlySerLeu
8821 GAGACTAAGTGCCCATGTGGTTATGAGATGAAAGCACTAAGGAACGTTAGTGGCAGTCTT
     CTCTGATTCACGGGTACACCAATACTCTACTTTCGTGATTCCTTGCAATCACCGTCAGAA

     ThrIleValGluGluLysGlyProPheLeuCysArgAsnArgProGlyArgGlyProVal
8881 ACTATAGTGGAAGAGAAAGGGCCTTTTCTCTGTAGGAACAGGCCTGGTAGAGGGCCAGTT
     TGATATCACCTTCTCTTTCCCGGAAAAGAGACATCCTTGTCCGGACCATCTCCCGGTCAA

     8920 stu1, 8938 hpa1,

     AsnTyrArgValThrLysTyrTyrAspAspAsnLeuAlaGluIleLysProValArgArg
8941 AACTATAGAGTTACAAAATACTATGATGACAACCTCGCAGAGATAAAGCCAGTTCGAAGA
     TTGATATCTCAATGTTTTATGATACTACTGTTGGAGCGTCTCTATTTCGGTCAAGCTTCT

     LeuGluGlyLeuValGluHisTyrTyrLysGlyValThrAlaArgIleAspTyrGlyLys
9001 CTAGAAGGACTCGTGGAGCACTATTACAAAGGTGTCACAGCAAGGATAGATTATGGCAAG
     GATCTTCCTGAGCACCTCGTGATAATGTTTCCACAGTGTCGTTCCTATCTAATACCGTTC

     GlyLysMetLeuLeuAlaThrAspLysTrpGluValGluHisGlyIleValThrArgLeu
9061 GGAAAAATGCTGTTAGCCACTGATAAATGGGAGGTGGAGCACGGTATCGTAACTAGGTTG
     CCTTTTTACGACAATCGGTGACTATTTACCCTCCACCTCGTGCCATAGCATTGATCCAAC

     AlaLysLysTyrThrGlyValGlyPheLysGlyAlaTyrLeuGlyAspGluProAsnHis
9121 GCGAAGAAGTACACTGGTGTTGGGTTCAAGGGAGCATACCTGGGTGACGAGCCCAACCAC
     CGCTTCTTCATGTGACCACAACCCAAGTTCCCTCGTATGGACCCACTGCTCGGGTTGGTG

     ArgAspLeuValGluArgAspCysAlaThrIleThrLysAsnThrValGlnPheLeuLys
9181 CGTGACCTAGTGGAAAGAGACTGTGCAACCATAACCAAAAATACAGTTCAGTTTTTGAAA
     GCACTGGATCACCTTTCTCTGACACGTTGGTATTGGTTTTTATGTCAAGTCAAAAACTTT
```

FIG.2N

MetLysLysGlyCysAlaPheThrTyrAspLeuSerLeuSerAsnLeuThrArgLeuIle
9241 ATGAAGAAAGGCTGTGCATTTACCTATGACTTGTCCCTGTCCAATTTGACCAGGTTAATT
TACTTCTTTCCGACACGTAAATGGATACTGAACAGGGACAGGTTAAACTGGTCCAATTAA

GluLeuValHisLysAsnAsnLeuGluGluLysAspIleProAlaAlaThrLeuThrThr
9301 GAATTGGTGCACAAAAATAACCTTGAAGAGAAAGACATACCAGCCGCCACATTAACAACA
CTTAACCACGTGTTTTTATTGGAACTTCTCTTTCTGTATGGTCGGCGGTGTAATTGTTGT

CysLeuAlaTyrThrPheValAsnGluAspIleGlyThrIleLysProValLeuGlyGlu
9361 TGCCTAGCTTACACATTTGTGAATGAAGATATCGGGACTATAAAACCAGTACTGGGGGAG
ACGGATCGAATGTGTAAACACTTACTTCTATAGCCCTGATATTTTGGTCATGACCCCCTC 9388 ecor5, 9408 scal, ArgValIleAlaAspProValValAspIleAsnLeuGlnProGluValGlnValAspThr
9421 AGAGTGATAGCCGACCCAGTGGTAGACATTAACTTACAACCAGAAGTGCAGGTGGATACA
TCTCACTATCGGCTGGGTCACCATCTGTAATTGAATGTTGGTCTTCACGTCCACCTATGT SerGluValGlyIleThrLeuValGlyArgAlaAlaLeuMetThrThrGlyIleThrPro
9481 TCAGAGGTTGGGATCACTCTGGTTGGAAGAGCAGCCTTGATGACAACAGGTATTACACCC
AGTCTCCAACCCTAGTGAGACCAACCTTCTCGTCGGAACTACTGTTGTCCATAATGTGGG ValValGluLysThrGluProAsnAlaAspGlySerProSerSerIleLysIleGlyLeu
9541 GTGGTTGAAAAAACAGAGCCTAATGCCGATGGCAGTCCAAGCTCTATAAAGATTGGACTG
CACCAACTTTTTTGTCTCGGATTACGGCTACCGTCAGGTTCGAGATATTTCTAACCTGAC AspGluGlyCysTyrProGlyProArgProGlnAspHisThrLeuAlaAspGluIleHis
9601 GACGAAGGATGTTACCCAGGGCCTAGACCGCAAGACCACACTTTAGCTGACGAAATACAT
CTGCTTCCTACAATGGGTCCCGGATCTGGCGTTCTGGTGTGAAATCGACTGCTTTATGTA SerArgAspGluArgProPheValLeuValLeuGlySerArgSerSerMetSerAsnArg
9661 TCTAGGGATGAAAGGCCCTTTGTTTTGGTCTTGGGTTCAAGAAGTTCCATGTCAAATAGA
AGATCCCTACTTTCCGGGAAACAAAACCAGAACCCAAGTTCTTCAAGGTACAGTTTATCT AlaLysThrAlaArgAsnIleAsnCysThrGlnLysArgProGlnGluIleArgAspLeu
9721 GCAAAAACTGCTAGAAACATCAACTGTACACAGAAAAGACCCCAGGAAATTAGAGATCTG
CGTTTTTGACGATCTTTGTAGTTGACATGTGTCTTTTCTGGGGTCCTTTAATCTCTAGAC 9774 bgl11, MetAlaGlnGlyArgMetLeuValValAlaLeuArgSerPheAsnProGluLeuSerGlu
9781 ATGGCACAAGGGCGTATGCTAGTAGTGGCTTTAAGAAGTTTCAATCCTGAGTTGTCTGAA
TACCGTGTTCCCGCATACGATCATCACCGAAATTCTTCAAAGTTAGGACTCAACAGACTT 9840 spel, LeuValAspPheLysGlyThrPheLeuAspArgValAlaLeuGluAlaLeuSerLeuGly
9841 CTAGTTGATTTCAAGGGGACTTTCTTGGATAGGGTTGCCTTGGAAGCCCTTAGCCTGGGG
GATCAACTAAAGTTCCCCTGAAAGAACCTATCCCAACGGAACCTTCGGGAATCGGACCCC 9900 bgl1, ProGlyArgProLysGlnValThrThrAlaThrValLysGluLeuLeuGluGlnGluGlu
9901 CCGGGAAGGCCCAAGCAGGTAACCACAGCCACAGTTAAGGAGTTGCTAGAGCAAGAGGAA
GGCCCTTCCGGGTTCGTCCATTGGTGTCGGTGTCAATTCCTCAACGATCTCGTTCTCCTT 9918 bstE2,

FIG.20

```
      GlnValGluIleProAsnTrpPheGlyAlaAspAspProValPheLeuGluValAlaLeu
9961  CAAGTCGAGATCCCCAACTGGTTCGGTGCGGATGACCCAGTCTTCTTGGAAGTAGCTCTG
      GTTCAGCTCTAGGGGTTGACCAAGCCACGCCTACTGGGTCAGAAGAACCTTCATCGAGAC
                                        ^
      9994 tthIII1,

      LysGlyAspLysTyrHisLeuValGlyAspValAspLysValLysAspGlnAlaLysGly
10021 AAGGGTGACAAATACCACTTAGTAGGTGATGTAGATAAAGTAAAAGATCAAGCAAAGGGA
      TTCCCACTGTTTATGGTGAATCATCCACTACATCTATTTCATTTTCTAGTTCGTTTCCCT

      LeuGlyAlaThrAspGlnThrArgIleValLysGluValGlyAlaArgThrTyrThrMet
10081 CTAGGGGCCACGGACCAAACTAGAATAGTAAAAGAAGTAGGTGCGAGAACCTACACAATG
      GATCCCCGGTGCCTGGTTTGATCTTATCATTTTCTTCATCCACGCTCTTGGATGTGTTAC

      LysLeuSerSerTrpPheLeuGlnAlaSerSerLysGlnMetSerLeuThrProLeuPhe
10141 AAGCTGTCTAGTTGGTTTCTTCAAGCATCAAGTAAACAGATGAGCTTGACCCCTTTGTTC
      TTCGACAGATCAACCAAAGAAGTTCGTAGTTCATTTGTCTACTCGAACTGGGGAAACAAG

      GluGluLeuLeuLeuArgCysProProLysMetLysAsnAsnLysGlyHisIleGlySer
10201 GAGGAACTGTTGCTTCGTTGCCCTCCCAAGATGAAGAACAATAAAGGGCATATCGGATCA
      CTCCTTGACAACGAAGCAACGGGAGGGTTCTACTTCTTGTTATTTCCCGTATAGCCTAGT

      AlaTyrGlnLeuAlaGlnGlyAsnTrpGluProLeuAspCysGlyValHisLeuGlyThr
10261 GCCTACCAACTAGCTCAGGGCAACTGGGAACCCCTCGATTGTGGAGTACACCTGGGCACC
      CGGATGGTTGATCGAGTCCCGTTGACCCTTGGGGAGCTAACACCTCATGTGGACCCGTGG

      IleProAlaArgArgValLysIleHisProTyrGluAlaTyrLeuLysLeuLysAspLeu
10321 ATACCTGCCAGGAGGGTAAAGATCCACCCATATGAGGCCTATCTGAAACTGAAGGATTTA
      TATGGACGGTCCTCCCATTTCTAGGTGGGTATACTCCGGATAGACTTTGACTTCCTAAAT
                                   ^     ^
      10349 ndel, 10355 stul,

      LeuGluGluGluGluArgLysProGluGlyArgAspThrValIleArgGluHisAsnLys
10381 TTAGAAGAAGAAGAGAGGAAGCCAGAGGGTAGAGATACAGTGATAAGAGAACATAACAAG
      AATCTTCTTCTTCTCTCCTTCGGTCTCCCATCTCTATGTCACTATTCTCTTGTATTGTTC

      TrpIleLeuLysLysValArgProProArgLysProGlnTyrLysGluAsnProGlnPro
10441 TGGATCCTCAAAAAAGTGAGGCCACCAAGGAAACCTCAATACAAAGAAAATCCTCAACCC
      ACCTAGGAGTTTTTTCACTCCGGTGGTTCCTTTGGAGTTATGTTTCTTTTAGGAGTTGGG
       ^
      10442 bamhl,

      TrpLysAlaIleArgAlaThrArgLeuGluLysGlyIleLysGluThrSerIleIleThr
10501 TGGAAAGCTATCAGAGCAACTAGACTAGAGAAGGGCATAAAAGAAACATCTATAATAACC
      ACCTTTCGATAGTCTCGTTGATCTGATCTCTTCCCGTATTTTCTTTGTAGATATTATTGG

      LysLeuAlaSerIleLeuThrGlyAlaGlyIleArgLeuGluLysLeuProValValArg
10561 AAATTGGCCTCCATACTAACAGGTGCAGGAATAAGGCTGGAAAAATTGCCAGTCGTTAGA
      TTTAACCGGAGGTATGATTGTCCACGTCCTTATTCCGACCTTTTTAACGGTCAGCAATCT

      AlaGlnThrAspHisLysSerPheHisGluAlaIleArgAspLysIleAspLysAsnGlu
10621 GCCCAAACTGACCATAAAAGTTTCCATGAGGCAATCAGAGATAAGATAGACAAGAACGAA
      CGGGTTTGACTGGTATTTTCAAAGGTACTCCGTTAGTCTCTATTCTATCTGTTCTTGCTT

      AsnGlnGlnSerProGlyLeuHisAspLysLeuLeuGluIlePheHisThrIleAlaGln
10681 AATCAGCAGAGCCCAGGATTACATGATAAATTGTTAGAGATCTTTCACACAATAGCCCAA
      TTAGTCGTCTCGGGTCCTAATGTACTATTTAACAATCTCTAGAAAGTGTGTTATCGGGTT
                                           ^
      10718 bglll,
```

FIG.2P

```
      ProSerLeuLysHisThrTyrGlyGluValThrTrpGluGlnLeuGluAlaGlyIleAsn
10741 CCCAGCCTAAAGCACACTTACGGCGAAGTGACGTGGGAACAGCTTGAGGCAGGGATCAAC
      GGGTCGGATTTCGTGTGAATGCCGCTTCACTGCACCCTTGTCGAACTCCGTCCCTAGTTG

      ArgLysGlyAlaAlaGlyPheLeuGluLysLysAsnLeuGlyGluValLeuAspSerGlu
10801 AGAAAAGGGGCTGCAGGCTTTCTAGAAAAGAAGAATCTTGGAGAAGTACTGGACTCAGAG
      TCTTTTCCCCGACGTCCGAAAGATCTTTTCTTCTTAGAACCTCTTCATGACCTGAGTCTC

      10811 pstl, 10821 xbal, 10845 scal,

      LysHisLeuValAspGlnLeuIleArgAspLeuLysThrGlyArgLysIleArgTyrTyr
10861 AAGCACCTGGTGGACCAACTAATCAGAGACCTGAAAACAGGACGGAAGATAAGATATTAT
      TTCGTGGACCACCTGGTTGATTAGTCTCTGGACTTTTGTCCTGCCTTCTATTCTATAATA

      GluThrAlaIleProLysAsnGluLysArgAspValSerAspAspTrpGlnAlaGlyAsp
10921 GAGACAGCAATACCTAAGAACGAGAAGAGGGATGTCAGTGACGATTGGCAAGCAGGGGAC
      CTCTGTCGTTATGGATTCTTGCTCTTCTCCCTACAGTCACTGCTAACCGTTCGTCCCCTG

      IleValAspGluLysLysProArgValIleGlnTyrProGluAlaLysThrArgLeuAla
10981 ATAGTTGATGAAAAGAAACCAAGAGTGATTCAATACCCTGAAGCTAAGACAAGACTGGCC
      TATCAACTACTTTTCTTTGGTTCTCACTAAGTTATGGGACTTCGATTCTGTTCTGACCGG

      11036 ball,

      IleThrLysValMetTyrAsnTrpValLysGlnGlnProValValIleProGlyTyrGlu
11041 ATCACTAAAGTTATGTACAACTGGGTGAAGCAGCAGCCTGTTGTGATCCCAGGGTATGAA
      TAGTGATTTCAATACATGTTGACCCACTTCGTCGTCGGACAACACTAGGGTCCCATACTT

      GlyLysThrProLeuPheLysIlePheAsnLysValArgLysGluTrpAspLeuPheAsn
11101 GGGAAGACCCCATTATTCAAGATCTTTAACAAGGTAAGAAAGGAATGGGACCTGTTCAAT
      CCCTTCTGGGGTAATAAGTTCTAGAAATTGTTCCATTCTTTCCTTACCCTGGACAAGTTA

      11120 bglll,

      GluProValAlaValSerPheAspThrLysAlaTrpAspThrGlnValThrSerArgAsp
11161 GAGCCAGTAGCTGTGAGTTTTGATACTAAGGCCTGGGACACCCAAGTCACTAGTAGGGAT
      CTCGGTCATCGACACTCAAAACTATGATTCCGGACCCTGTGGGTTCAGTGATCATCCCTA

      11189 stul, 11209 spel,

      LeuArgLeuIleGlyGluIleGlnLysTyrTyrTyrArgLysGluTrpHisLysPheIle
11221 CTACGGCTTATTGGTGAAATTCAAAAATATTACTACAGGAAGGAGTGGCACAAATTCATC
      GATGCCGAATAACCACTTTAAGTTTTTATAATGATGTCCTTCCTCACCGTGTTTAAGTAG

      11246 sspl, 11278 clal,

      AspThrIleThrAspHisMetValGluValProValIleThrAlaAspGlyGluValTyr
11281 GATACCATCACCGACCACATGGTGGAGGTACCAGTCATAACAGCAGATGGTGAAGTATAC
      CTATGGTAGTGGCTGGTGTACCACCTCCATGGTCAGTATTGTCGTCTACCACTTCATATG

      11307 kpnl,

      IleArgAsnGlyGlnArgGlySerGlyGlnProAspThrSerAlaGlyAsnSerMetLeu
11341 ATAAGAAATGGACAAAGGGGTAGTGGCCAGCCAGACACAAGCGCAGGTAACAGCATGCTA
      TATTCTTTACCTGTTTCCCCATCACCGGTCGGTCTGTGTTCGCGTCCATTGTCGTACGAT

      11364 ball, 11393 sphl,
```

FIG.2Q

```
      AsnValLeuThrMetMetTyrAlaPheCysGluSerThrGlyValProTyrLysSerPhe
11401 AATGTGTTAACAATGATGTATGCCTTCTGTGAAAGTACGGGGGTTCCATATAAGAGTTTT
      TTACACAATTGTTACTACATACGGAAGACACTTTCATGCCCCCAAGGTATATTCTCAAAA
           ^
      11406 hpal,

      AsnArgValAlaArgIleHisValCysGlyAspAspGlyPheLeuIleThrGluArgGly
11461 AATAGAGTTGCAAGGATCCATGTCTGTGGGGATGACGGCTTCCTGATAACAGAGAGGGGG
      TTATCTCAACGTTCCTAGGTACAGACACCCCTACTGCCGAAGGACTATTGTCTCTCCCCC
                   ^   ^
      11474 bamhl, 11478 bstXI,

      LeuGlyThrLysIleCysGlnGlnArgAspAlaAsnPheCysMetArgArgAlaSerSer
11521 CTGGGCACTAAAATTTGCCAACAAAGGGATGCAAACTTCTGCATGAGGCGGGCAAGCTCA
      GACCCGTGATTTTAAACGGTTGTTTCCCTACGTTTGAAGACGTACTCCGCCCGTTCGAGT

      LysAsnAsnArgArgGlyLysAsnGluSerLeuProIleGlyLeuArgHisArgValLeu
11581 AAAAATAACAGAAGGGGAAAGAATGAAAGCTTGCCTATAGGTTTGAGGCATAGAGTTTTG
      TTTTTATTGTCTTCCCCTTTCTTACTTTCGAACGGATATCCAAACTCCGTATCTCAAAAC
                                ^
      11607 hindlll,

      LeuProHisThrSerProArgLysCysLeuIleIleProAlaAlaThrTrpProValGly
11641 CTCCCACACACCAGTCCCCGTAAGTGTCTGATAATACCAGCAGCTACATGGCCGGTAGGC
      GAGGGTGTGTGGTCAGGGGCATTCACAGACTATTATGGTCGTCGATGTACCGGCCATCCG

      ThrAlaIleIleLeuSerLysMetAlaAsnLysIleGlyLeuSerGlyGluArgGlyThr
11701 ACTGCCATTATATTATCAAAGATGGCCAACAAGATTGGATTAAGTGGAGAGAGAGGTACC
      TGACGGTAATATAATAGTTTCTACCGGTTGTTCTAACCTAATTCACCTCTCTCTCCATGG
                            ^                               ^
      11723 ball, 11755 kpnl,

      ThrAlaTyrGluLysAlaValAlaPheSerPheLeuLeuMetTyrSerTrpAsnProLeu
11761 ACGGCATATGAAAAGGCAGTGGCTTTCAGTTTCTTGTTGATGTACTCCTGGAATCCACTT
      TGCCGTATACTTTTCCGTCACCGAAAGTCAAAGAACAACTACATGAGGACCTTAGGTGAA
          ^
      11765 ndel,

      ValArgArgIleCysLeuLeuValLeuSerGlnHisProGluThrAlaProSerThrGln
11821 GTAAGGAGGATTTGTCTCCTGGTTCTTTCACAGCATCCAGAAACAGCTCCATCAACCCAG
      CATTCCTCCTAAACAGAGGACCAAGAAAGTGTCGTAGGTCTTTGTCGAGGTAGTTGGGTC

      ThrSerTyrTyrTyrLysGlyAspProIleGlyAlaTyrLysAspValIleGlyLysAsn
11881 ACCTCTTACTATTATAAAGGAGACCCAATAGGGGCCTATAAAGATGTTATAGGAAAAAAT
      TGGAGAATGATAATATTTCCTCTGGGTTATCCCCGGATATTTCTACAATATCCTTTTTTA

      LeuSerGluLeuLysArgThrGlyPheGluLysLeuAlaAsnLeuAsnLeuSerLeuSer
11941 CTGAGTGAACTAAAAAGGACGGGTTTTGAAAAATTGGCTAATCTAAATCTAAGCCTGTCC
      GACTCACTTGATTTTTCCTGCCCAAAACTTTTTAACCGATTAGATTTAGATTCGGACAGG

      ThrLeuGlyIleTrpSerLysHisThrSerLysArgIleIleGlnAspCysValThrIle
12001 ACACTAGGAATCTGGTCCAAACATACAAGTAAACGAATAATCCAGGACTGTGTAACCATC
      TGTGATCCTTAGACCAGGTTTGTATGTTCATTTGCTTATTAGGTCCTGACACATTGGTAG

      GlyLysGluAspGlyAsnTrpLeuValAsnAlaAspArgLeuIleSerSerLysThrGly
12061 GGGAAAGAGGACGGCAATTGGCTGGTAAATGCCGACAGGCTGATATCAAGCAAAACTGGC
      CCCTTTCTCCTGCCGTTAACCGACCATTTACGGCTGTCCGACTATAGTTCGTTTTGACCG
                                               ^              ^
      12102 ecor5, 12117 ball,
```

FIG.2R

```
      HisLeuTyrIleProAspLysGlyTryThrLeuGlnGlyLYsHisTyrGluGlnLeuGln
12121 CATCTGTACATACCTGACAAAGGTTATACATTACAGGGAAAACACTATGAACAACTTCAA
      GTAGACATGTATGGACTGTTTCCAATATGTAATGTCCCTTTTGTGATACTTGTTGAAGTT

      12169 xmnl,

      LeuGlnAlaArgThrSerProIleMetGlyValGlyThrGluArgTyrLysLeuGlyPro
12181 TTGCAGGCAAGAACTAGCCCAATCATGGGAGTAGGGACAGAGAGATATAAACTAGGTCCT
      AACGTCCGTTCTTGATCGGGTTAGTACCCTCATCCCTGTCTCTCTATATTTGATCCAGGA

      IleValAsnLeuLeuLeuArgArgLeuLysValLeuLeuMetAlaAlaValGlyAlaSer
12241 ATAGTAAACTTGCTGCTGAGGAGGTTGAAAGTCCTGCTTATGGCAGCTGTCGGTGCCAGC
      TATCATTTGAACGACGACTCCTCCAACTTTCAGGACGAATACCGTCGACAGCCACGGTCG

      12284 pvull,

      SerOP
12301 AGTTGAAATAAATGTATATATTGTACATAAATCTGTATTTGTATATATTATATATAAACT
      TCAACTTTATTTACATATATAACATGTATTTAGACATAAACATATATAATATATATTTGA

12361 TAGTTGAGATTAGTAGTGATATATAGTTATCTACCTCAAGTAAACACTACACTCAATGCA
      ATCAACTCTAATCATCACTATATATCAATAGATGGAGTTCATTTGTGATGTGAGTTACGT

12421 CACAGCACTTTAGCTGTATGAGGGAACACCCGACGTCCATGGTTGGACTAGGGAAGACCC
      GTGTCGTGAAATCGACATACTCCCTTGTGGGCTGCAGGTACCAACCTGATCCCTTCTGGG

      12452 aatII, 12457 ncol,

12481 TTAACAGCCCCA
      AATTGTCGGGGT
```

FIG.2S

DNA ENCODING BOVINE DIARRHEA VIRUS PROTEIN

This application is a continuation of application Ser. No. 07/331,037, filed 29 Mar. 1989, now abandoned, which is a continuation of application Ser. No. 06/752,981, filed 8 Jul. 1985, now abandoned.

TECHNICAL FIELD

This invention relates to the field of vaccines and diagnostics for infectious diseases. Specifically, it relates to the disease syndrome caused by bovine diarrhea virus, and to vaccines, therapeutics, and diagnostics derived from the genomic sequence associated with the BDV virus.

BACKGROUND ART

Morbidity and mortality caused by bovine diarrhea virus (BDV) in dairy and beef herds is a worldwise unsolved economic problem. A subclinical form characterized by high morbidity and low mortality is endemic and is associated with diminished respiratory capacity, neonatal diarrhea, ulcerations in the digestive tract, immunodeficiency, and, in calf bearing bovines, abortion teratogenicity. The disease is recognizable in claves, but adult carriers are difficult to identify.

An acute form of the disease results from infection of the fetus in the first trimester of pregnancy. The course of this form of the disease is insidious. The claves may survive the first infection, but those that do become immunotolerant, and excrete live viruses. They cannot survive a second infection. Since their capacity as carriers cannot be detected by titration of their sera, these animals are responsible for spreading of the disease from herd to herd.

BDV also infects hog populations. In hogs, it is important to distinguish animals as being infected by either BDV or hog chlorea virus, since hog cholera is an economically important disease, while the bovine diarrhea infection is of transient significance, and could, for the most part, be ignored. Hogs infected with cholera must be slaughtered, and since present diagnostic methods in hogs cannot distinguish between these two types of infection, hogs which are, in fact, only infected with BDV must also be destroyed.

Present means of detection of BDV infection in claves are equally deficient, in that they rely on titration for antibodies in sera, which titration will fail to detect the immunotolerant calves. Thus, a diagnostic method is desired, but presently unavailable, which is capable both of detecting the presence of the virus in newborn animals with chronic infections, and in distinguishing between hog cholera virus and BDV infections. This could be accomplished either using antibodies with high affinity and specificity for the virus particles or using nucleic acid oligomeric probes capable of specific hybridization to the viral sequences.

Similarly, in addition to the need for improved diagnostics, there is, at present, no effective vaccine which is successful in preventing the spread of the disease caused by BDV. It is, of course, desirable that such a vaccine would confer long-term immunity, would not infect the fetus of the inoculated animal, and would have no undesirable side effects such as induction of immunotolerance to the virus, or depression of the immune system. These characteristics are difficult if not impossible to acquire in an attenuated or killed virus vaccine. Such vaccines, for the most part, constitute the present state of the art (Saurat, P., et al. 'La Maladie des Muqueuses" (1972) pp. 229-251, *L'Expansion scientific francaise* Paris). Recently, Fernelius, A. L., et al. (*am J Vet Res* (1971) 32:1963-1979) have reported a vaccine prepared from a high molecular weight soluble antigen obtained by density gradient centrifugation from BDV virus grown in embryonic bovine kidney cells.

The approaches used in the art for the detection of and protection against bovine viral diarrhea have been largely empirical and have not utilized refined knowledge of the nature of the vector causing the disease. The bovine diarrhea virus has, however, been classified, along with hog cholera and border disease viruses as a pestivirus which is a member of the family Togaviridae (Porterfield, J. S., "the Togavirions. Biology, Structure, Replication" Schlesinger, W., Ed. (1980), Academic Press, pp. 17-24).

By analogy to other togaviruses, these viruses should contain a capsid protein and two or three membrane glycoproteins (Horzinek, M.C., *Non-arthropod borne Togaviruses* (1981). Academic Press, London.) Epitopes which are capable of raising antibodies associated with neutralization and protection against infection are expected to be contained in the membrane proteins (e.g., see Boere, W., et al., *J Virol* (1984) 52:572-582). The pestiviruses are also characterized by soluble antigen that are approximately 80 kD proteins. A 76 kD protein from BDV has, in fact, been used as an experimental vaccine (Fernelius, A. L., et al. supra).

DISCLOSURE OF THE INVENTION

The invention provides cDNA copies of the entire bovine diarrhea virus RNA genomic sequence. This makes available the entire repertoire of peptides synthesized by the virus, and makes possible the preparation of proteins which contain epitopes effective and specific in generating desired antibodies and, in providing cells suitable for production of monoclonal antibodies. The primary structure of the genome also provides the necessary information to construct oligomeric sequences useful as diagnostic probes.

The protein products are thus able to serve as vaccines to protect animals subject to infection by this virus from subsequent illness. The accessibility of the entire genome provides opportunities for production of effective proteins, such as major virion components and individual virion subunits which would be unavailable using "antive" production techniques, i.e., from viral infection of tissue cultured cells.

Accordingly, in one aspect, the invention relates to a necleotide sequence substantially identical with that representing the entire genome of BDV as shown in FIG. 2. Other aspects of the invention concern DNA or RNA sequences derived from portions of the genome, said sequences not necessarily representing contiguous portions. These are useful both as diagnostic probes and as coding sequences for desired proteins.

Other aspects of the invention include expression systems for the foregoing DNA derived from BDV which ar effective in expressing this DNA in suitable heterologous hosts, including procaryotes, yeast, and mammalian cells. Live viral vectors, such as vaccinia, can also be used as carriers, and permit expression of the desired antigen along with the carriers' proteins in infected cells. Also included in the invention are hosts transformed with these expression systems and the proteins thus produced. The proteins produced in this way, or chemically synthesized to correspond to the deduced sequence, may be used as vaccines either alone, or in conjunction with carrier proteins which enhance their immunogenicity. In addition, the proteins may be used, either alone or conjugated with carrier, to elicit production of antibodies which are useful in diagnosis of carriers of the disease or in other immunoassays related to BDV.

The invention also relates to methods for preparing these polypeptide vaccines and immunoglobulins, and to methods of using the materials thus prepared.

BRIEF DESCRIPTION OF THE DRAWINGS

FIG. 2 (parts A-S) shows the complete nucleotide sequence for the BDV genome. The cDNA contains the identical sequence, except, of course, that T will be substituted for U. The deduced amino acid sequence, based on the open reading frame, and confirmed by expression of segments is also shown.

MODES OF CARRYING OUT THE INVENTION

A. Definitions

Figure 1:
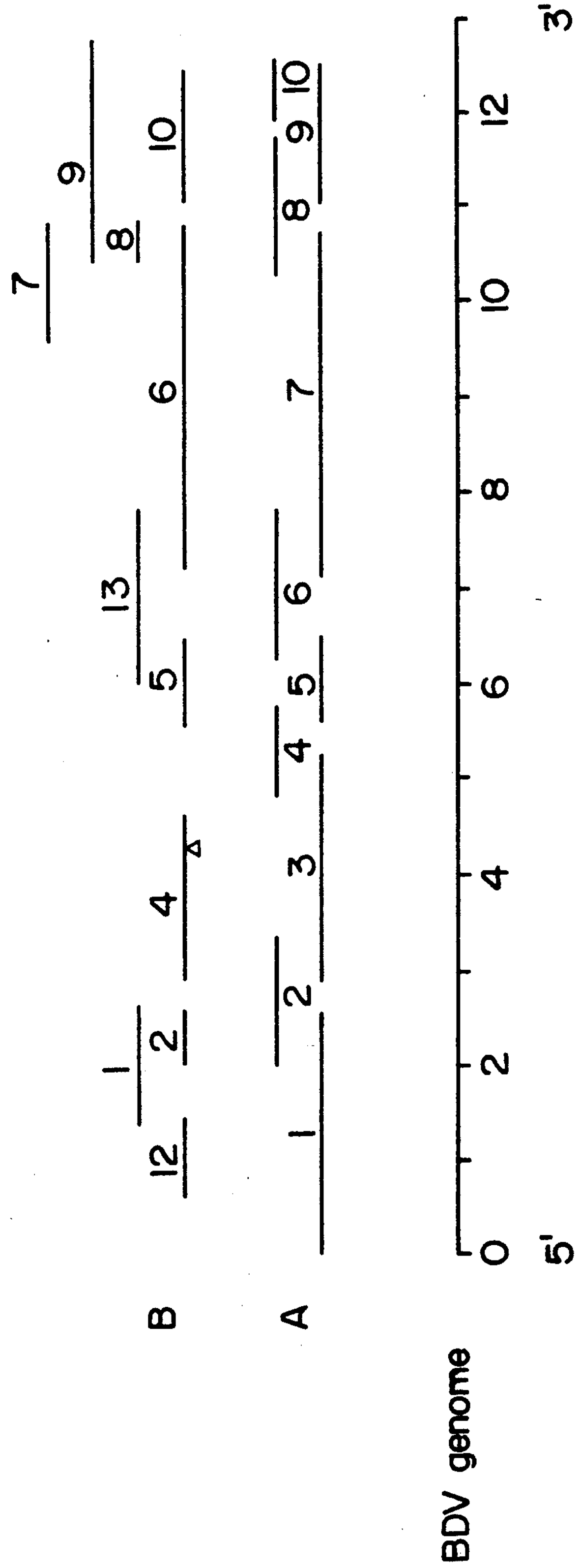
FIG. 1 shows the map of overlapping segments of cDNA which, together, make up the entire BDV genomic sequence and cDNA fragments used to construct *E. coli* expression vectors.

As used herein, a nucleotide sequence "substantially identical " to the exemplified BDV genome refers to a sequence which retains the essential properties of the exemplified polynucleotide. A specific, but non-limiting example of such substantial equivalence would be represented by a sequence which encodes the identical or substantially identical amino acid sequence, but, which, because of codon degeneracy, utilizes different specific codons. Nucleotide changes are, indeed, often desirable to create or delete restrictions sites, provide processing sites, or to alter the amino acid sequence in ways which do not adversely affect functionality. "Nucleotide sequence" refers both to a ribonucleotide and a deoxyribonucleotide sequence and includes the positive sense strand, as shown, and the negative sense strand as well.

A DNA sequence "derived from " the nucleotide sequence which comprises the genome of BDV refers to a DNA sequence which is comprised of a region of the genomic nucleotide sequence, or a combination of regions of that sequence. These regions are, of course, not necessarily physically derived from the nucleotide sequence of the gene, but refer to polynucleotides generated in whatever manner which have the same or "substantially identical" sequence of bases as that in the region(s) from which the polynucleotide is derived. For example, typical DNA sequences "derived from" the BDV genome include fragments encoding specific epitopes, fragments encoding portions of the viral polypeptide, sequences encoding the capsid proteins, sequences encoding deleted virions, and sequences encoding other useful viral amino acid sequences.

"Recombinant host cells", "host cells", "cells", "cell lines", "cell cultures", and other such terms denoting microorganisms or higher eucaryotic cell lines cultured as unicellular entities, are used interchageably, and refer to cells which can be, or have been, used as recipients for recombinant vector or other transfer DNA, and include the progeny of the original cell transfected. It is understood that the progeny of a single parental cell may not necessarily be completely identical in morphology or in genomic or total DNA complement as the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

"Control sequence" refers to DNA sequences which are necessary to effect the expression of coding sequences to which they are ligated. The nature of such control sequences differs depending on the host organism: in procaryotes, generally such control sequences include a regulatory region promoter and ribosome binding site and termination signals; in eucaryotes, generally, such control sequences include promoter, terminators, and, in some instances, transcriptional enhancers. The term "control sequences" is intended to include, at a minimum, all components which presence is necessary for expression, and may also include additional components whose presence is advantageous.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

B. General Description

At the center of the present invention is the provision of a nucleotide sequence containing the entire genome of bovine diarrhea virus. The availability of this complete polynucleotide permits the design and production of oligomeric probes for diagnosis, of vaccines effective against BDV, and of proteins useful in production of neutralizing antibodies. Sequencing information available from the genome allows the amino acid sequence of the polypeptide to be deduced, and locations of favorable epitopes surmised. Further, once the desired sequences are chosen, appropriate fragments of the genome can be obtained and expressed independently, thus providing desired polypeptides. Short polypeptide fragments may also be chemically synthesized and linked to carrier proteins for use as immunogens. Recombinantly expressed polypeptides may be provided under conditions offering a favorable environment for processing into, for example, conjugation with cellular or artificial membranes which could thus bear the epitopic sites without the disadvantages of using an infectious virus. Mammalian and yeast cells provide suitable environments for such expression. In addition, the epitopes may be produced linked to a particle forming protein.

The above proteins produced may, themselves be used as vaccines, or may be used to induce immunocompetent B cells in hosts, which B cells can then be used to produce hybridomas that secrete antibodies useful in passive immunotherapy and diagnosis.

B.1. Nucleotide Sequence of the BDV Genome

The genomic sequence of BDV was obtained from cDNA clones representing overlapping sections of the entire viral RNA genome (FIG. 1). The viral RNA was isolated from virus grown on bovine embryonic kidney cells. The viral RNA was fractionated on sucrose gradients, and those fractions containing RNA of sufficient length to contain the intact genome were pooled, ethanol precipitated, and used to prepare a cDNA library. cDNA inserts were screened initially using a (+/−) system. Positive hybridizations were against RNA isolated from virus after lysis of infected cells, negative hybridizations were against RNA isolated from uninfected cells. One insert having the proper +/− response was then used as a reference clone to map the remainder of the library. Several colonies hybridizing to the positive insert were used to obtain additional portions of the viral genome from the cDNA library using "walking" techniques. Ten cDNA clones were obtained representing overlapping portion of the viral genome, as shown in FIG. 1, and were subjected to restriction mapping and sequencing. The entire genomic sequence was deduced from these ten cDNA inserts, and is shown in FIG. 2.

The illustrated DNA sequence and portions thereof are useful directly as diagnostic tools for detecting the presence of BDV in infected animals. These are particularly useful in distinguishing BDV infections from hog cholera virus. Methods to employ DNA hybridization in diagnosing disease have been disclosed in U.S. Pat. No. 4,358,535 to Falkow. As set forth therein, biological samples may be used directly in obtaining Southern blots using suitable probes. Since the BDV genome is different from that of hog cholera virus, specific portions of the BDV sequence may be used to detect the presence of corresponding complementary sequences in biological samples from subjects suspected of harboring the infection.

B2. Preparation of Viral Polypeptide Fragments in *E. coli*

The availability of the entire genomic sequence permits construction of expression vectors encoding presumptively antigenically active regions of the virion proteins. Fragments encoding the desired proteins are obtained from the cDNA clones using conventional restriction digestion and ligated into a series of vectors containing polylinker sites in all possible reading frames to generate fusion proteins at the C-terminal end of $\beta$-galactosidase. Eleven portions of the BDV genome were expressed s $\beta$-gal fusions in *E. coli* using this approach, as outlined in FIG. 1 These portions were obtained by restriction cleavage and/or ligation of the ten original clones, or the original cloned sequences were used directly. The fusion proteins thus produced may be immunogenic.

B.3. Preparation of Antigenic Polypeptides and Conjugation with Carrier

Peptide regions representing epitopes can be synthesized using chemical or recombinant methods, and provided with, for example, cysteine residues at the C-terminus which provide means for linking the peptides to neutral carrier proteins. A number of techniques for obtaining such linkage are known in the art, including the formation of disulfide linkages using common reagents such as N-succinimidyl-3-(2-pyridyldithio) propionate (SPDP) and succinimidyl-4-(N-maleimidomethyl) cyclohexane-1-carboxylate (SMCC) obtained from Pierce Company, Rockford, Ill. These reagents create a disulfide linkage between themselves and peptide cysteine residues in one protein and an amide linkage through the $\epsilon$-amino on a lysine, or other free amino group in the other. A variety of such disulfide/amide-forming agents are known. See, for example, *Immun Rev* (1982) 62:185. Other bifunctional coupling agents form a thioethr rather than a disulfide linkage. Many of these thioether-forming agents are commercially available and include reactive esters of 6-maleimidocaproic acid, 2-bromoacetic acid, 2-iodoacetic acid, 4-(N-maleimido-methyl) cyclohexane-1-carboxylic acid, and the like. The carboxyl groups can be activated by combining them with succinimide or 1-hydroxy-2-nitor-4-sulfonic acid, sodium salt. The foregoing list is not meant to be exhaustive, and modifications of the named compounds can clearly be used.

Any carrier may be used which does not itself induce the production of antibodies harmful to the subject, such as the various serum albumins, tetanus toxoids, or keyhole limpet hemocyanin (KLH).

The conjugates, when injected into suitable subjects, result in the production of antisera which contain immunoglobulins specifically reactive against not only these conjugates, but also against fusion proteins carrying the analogous portions of the sequence, and against whole BDV.

B.4. Preparation of Mammalian Cell Membranes Containing BDV Epitopes

Portions of the cDNA library comprising the BDV genome were also ligated into expression vectors compatible with mammalian recombinant host cells; in the illustration below, into a mammalian/bacterial shuttle vector containing a linker sequence downstream of the SV40 early promoter, which i followed by the polyA sequence also derived from SV40. Alternate vectors to this particular host vector, pSV7d, could, of course, also be used. The mammalian-compatible vectors containing the coding sequences for the desired polypeptides are then transformed into suitable mammalian cells for expression of the sequences and, in the case of surface glycoproteins, transport of the produced protein to the membrane. The cells are ultimately harvested and used as whole cells in the formulation of vaccines, or the membranes are disrupted and portions of the membranes used correspondingly, or the proteins purified and formulated into vaccines.

B.5. Preparation of Hybrid Particle Immunogens Containing BDV Epitopes

The immunogenicity of the epitopes of BDV may also be enhanced by preparing them in mammalian or yeast systems fused with particle-forming proteins such as that associated with hepatitis B virus (HBV) surface antigen (HBsAg). Constructs wherein a BDV epitope is linked directly to the particle-forming protein coding sequences produce hybrids which are immunogenic with respect to the BDV epitope, as well as to HBV epitopes.

Hepatitis B surface antigen has been shown to be formed and assembled in *S. cerevisiae* (Valenzuela et al. *Nature* (1982)298:344–350. The formation of such particles has been shown to enhance the immunogenicity of the monomer subunit. The particles can also be formed from construct which contain the presurface (pre-S) region in addition to the mature surface antigen. The pre-S region encodes an immunodominant HBV epitope and these proteins are expressed in yeast (Neurath et al. *Science* (1984) 224:392–394). Expression of constructs incoding pre-S region fused to particle forming protein are disclosed in U.S. Ser. No. 621,756, filed 18 Jun. 1984. Expression of coding sequences for hybrid particles containing HBsAg and a heterologous epitope are disclosed in U.S. Ser. No. 650,323, filed 13 Sep. 1984. The foregoing applications are assigned to the herein assignee and incorporated by reference. These constructs may also be expressed in mammalian cells such as Chinese hamster ovary cells using an SV40-dihydrofolate reductase vector (Michelle et al. *Int Symp on Viral Hepatitis* (1984)).

In addition, portions of the particle-forming protein coding sequence per se may be replaced with codons for an BDV epitope. In this replacement, regions which are not required to mediate the aggregation of units to form immunogenic particles in yeast or mammals can be deleted, thus eliminating additional hepatitis B antigenic sites from competition with the BDV epitope.

B.6. Vaccinia Carrier

Large, wide host range virus carriers have also been used in formulating vaccines by integrating the epitopic regions of the desired immunogen into the carrier viral genome. Vaccinia virus, in particular, has been used for this purpose. For example, Smith, G. L., et al., *Proc Natl Acad Sci* (USA (1983) 80:7155–7159, disclose the integration of the hemagglutinin gene from influenza virus into the vaccinia genome and use of the resulting recombinant virus as a vaccine. Similarly, panicali, D., et al, ibid (1982)79:4927–4931, cloned the thymidine kinase gene from *Herpes simplex* virus into vaccinia. The availability of the BDV genome of the invention offers similar opportunities. The recombination is generally done by co-infecting cells both with vaccinia virus and with a chimeric plasmid carrying the desired coding sequence under the control of the transcriptional regulatory signals and RNA start site from the vaccinia virus gene adjacent to a translational start site/foreign protein coding sequence. During infection the similarity in the flanking DNA sequences of the foreign DNA sequences to those in vaccinia causes integration of the desired portion of the chimeric plasmid into the vaccinia genome. The resulting recombinant vaccinia can be harvested from the infected cells and use din the formulation of a vaccine. Vaccinia virus has an extremely large ($120X10^6$ dalton) genome, and may be very easily grown in culture. Hence, the production of large amounts of inexpensive immunogenic vaccine is readily possible.

B.7. Preparation of Vaccines

Preparation of vaccines which contain peptide sequences as active ingredients is also well understood in the art. Typically, such vaccines are prepared as injectables, either as liquid solutions or suspensions; solid forms suitable for solution in, or suspension in, liquid prior to injection may also be prepared. The preparation may also be emulsified or the protein encapsulated in liposomes. The active immunogenic ingredient is often mixed with excipients which are pharmaceutically acceptable and compatible with the active ingredient. Suitable excipients are, for example, water, saline, dextrose, glycerol, ethanol, or the like and combination thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkanine glycols or triglycerides; such suppositories may be formed from mixtures containing the active ingredient in the range of 0.5% to 10%, preferably 1%–2%. Oral formulations include such normally employed excipitents as, for example, pharmaceutical grades of manitol, lactose, starch magnesium stearate, sodium saccharine, cellulose, magnesium carbonate and the like. Thee compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts, include the acid addition salts (formed with the free amino groups of the peptide) and which are formed with inorganic acids such as, for example hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each subject.

B.8. Preparation of Mabs Against BDV Eptiopes

The immunogenic proteins or immunoconjugates prepared as described above may be used to obtain peripheral blood lymphocytes and spleen cells in injected mammals to prepare hybridomas capable of secreting monoclonal antibodies directed against these epitopes. The resulting monoclonal antibodies are particularly useful in diagnosis, and, those which are neutralizing are useful in passive immunothrapy.

C. General Methods

The general techniques used in extracting RNA from the virus, preparing and probing a cDNA library, sequencing clones, constructing expression vectors, transforming cells, and the like are known in the art and laboratory manuals are available describing these techniques. However, as a general guide, the following sets forth some sources currently available for such procedures, and for materials useful in carrying them out.

C.1. Hosts and Expression Control Sequences

Both procaryotic and eucaryotic host cells may be used for expression of desired coding sequences when appropriate control sequences are used compatible with the designated host. Procaryotes are more useful for cloning; either procaryotes or eucaryotes may be used for expressing. Among procaryotic hosts, *E. coli* is most frequently used mostly for convenience. Expression control sequences for procaryotes include promoters, optionally containing operator portions, and ribosome binding sites. Transfer vectors compatible with procryotic hosts are commonly derived from, for example, pBR322, a plasmid containing operons conferring ampicillin and tetracycline resistance, and the various pUC vectors, which also contain sequences conferring antibiotic resistance. The foregoing operons may be used as markers to obtain successful transformants by selection. Commonly used procaryotic control sequences include the B lactamase (penicillinase) and lactose promoter systems (Chang, et al., *Nature* (1977) 198:1056, the tryptophan (trp) promoter system (Goeddel, et al, *Nucleic Acids Res* (1980) 8:4057) and the λ derived $P_L$ promoter and N gene ribosome binding site (Shimatake, et al, *Nature* (1981) 292:128). The foregoing systems are particularly compatible with *E. coli;* if desired other procaryotic hosts such as strains of Bacillus or Pseudomonas may be sued, with corresponding control sequences.

Eucaryotic hosts include yeast and mammalian cell culture. *Saccharomyces cerevisciae,* or Baker's yeast and *Saccharomyces carlsbergensis* are the most commonly used yeast hosts, again because of convenience. Yeast compatible vectors carry markers which permit selection of successful transformants by conferring prototrophy to auxotrophic mutants or by conferring antiobiotic resistance or resistance to heavy metals on wild-type strains. Yeast compatible vectors may employ the 2 micron origin of replication (Broach, J., et al, *Meth Enz* (1983) 101:307) the combination of CEN3 and ARS1, or other means for assuring replication, such as sequences which will result in incorporation of the appropriate fragment into the host cell genome. Control sequences for yeast vectors include promoters for the synthesis for glycolytic enzymes (Hess, et al. *J. Adv Enzyme Reg* (1968) 7:149, Holland, et al, *Biochemistry* (1978) 17:4900), and the promoter for 3 phosphoglycerate kinase (hitzeman, et al. *J Biol Chem* (1980) 255:2073). For yeast expression, terminators may also be included, such as those derived from the enolase gene (Holland, M. J., *J Biol Chem* (1981) 256:1385). Particularly useful control systems include those specifically described herein, which comprise the glyceraldehyde-3 phosphate dehydrogenase (GAPDH) promoter or alcohol dehydrogenase (ADH) regulatable promoter, terminators also derived from GAPDH, and, if secretion is desired, leader sequence from yeast alpha factor. These systems are described in detail in U.S. Ser. Nos. 468,589 and 522,909, filed 22 Aug. 1983 and 12 Aug. 1983, respectively, assigned to the same assignee, and incorporated herein by reference.

Mammalian cell lines available as hosts for expression include many immortalized cell lines available from the American Type Culture Collection, including HeLa cells, Chinese hamster ovary (CHO) cells, baby hamster kidney (BHK) cells, and a number of other cell lines. Suitable promoters for mammalian cells prominently include viral promoters such as that from Simian virus 40 (SV40) (Fiers, et al, *Nature* (1978) 273:113) or other viral promoters such as the Ropus sarcoma virus (RSV) adenovirus, and bovine papiloma virus (BPV). Mammalian cells may also require terminator sequences. Vectors suitable for replication in mammalian cells may include viral replicons, or sequences which insure integration of the appropriate sequences into the host genome.

C.2. Transformations

The transformation procedure used depends on the host to be transformed. Bacterial transformation generally employs treatment with calcium or rubidium chloride (Cohen, S. N., *Proc Natl Acad Sci* (USA) (1972) 69:2110, Maniatis, et al, *Molecular Cloning: A Laboratory Manual* (1982) Cold Spring Harbor Press. p. 254). Yeast transformations may be carried out using the method of Hinnen, A., et al, *Proc Natl Acad Sci* (USA) (1978) 75:1929–1933. Mammalian transformations are conducted using the calcium phosphate precipitation method of Grahm and van der Eb. *Virology* (1978) 52:546, or the various modifications thereof.

C.3. Vector Construction

Vector construction employs techniques which are by now quite well understood. Site-specific DNA cleavage is performed by treating with suitable restriction enzyme under conditions which generally are specified by the manufacturer of these commercially available enzymes (see e.g., The New England Bilabs Product Catalog). In general, about 1 μg of plasmid or DNA sequence is cleaved by 1 unit enzyme in about 20 μl buffer solution for an incubation time of about 1–2 hr at about 37° C. After incubation with the restriction enzyme, protein is removed by phenol/chloroform extraction and the DNA recovered by reprecipitation with ethanol. The cleaved fragments may be separated using polyacrylamide or agarose gel electrophoresis techniques, according to the general procedures found in *Methods in Enzymology* (1980) 65:499–560.

Sticky ended cleavage fragments may be blunt ended using *E. coli* DNA polymerase I (Klenow) in the presence of the appropriate deoxynucleotide triphosphates (dNTPs) using incubation conditions appropriate to the polymerase. The polymerase digests protruding 3′ single strands, but fills in 5′ protruding ends, according to the dNTPs present in the mixture. Treatment with S1 nuclease may also be used, as this results in hydrolysis of any single stranded DNA portion.

Ligations are carried out using standard buffer and temperature conditions using T4 DNA ligase, and ATP; sticky end ligations require less ATP and less ligase than blunt end ligations. When vector fragments are used as part of a ligation mixture, the vector fragment is often treated with bacterial alkaline phosphatase (BAP) in order to remove the 5′ phosphate and thus present religation of the vector; alternatively, restriction enzyme digestion of unwanted fragments can be used to prevent religation.

Ligation mixtures are transformed into suitable cloning hosts, such as *E. coli*, and successful transformants selected by, for example, antibiotic resistance, and screened for the correct construction.

C.4. Construction of Desired DNA Sequences

Synthetic oligonucleotides may be prepared using an automated oligonucleotide synthesizer as described by Warner, B. D., et al. *DNA* (1984) 3:401-411. If desired, these synthetic strands may be kinased for labeling with $^{32}P$ by using an excess of polynucleotide kinase in the presence of labeled ATP, under standard kinasing conditions.

DNA sequences including those isolated from genomic or cDNA libraries may be modified by site directed mutagenesis, s described by Zoller, M, et al, *Nucleic Acids Res* (1982) 10:6487–6499. Briefly, the DNA to be modified is packaged into phage as a single stranded sequence, and converted to a double stranded DNA with DNA polymerase using, as a primer, a synthetic oligonucleotide complementary to the potion of the DNA to be modified, and having the desired modification included in its own sequence. The resulting double stranded DNA is transformed into a phage supporting host bacterium, and cultures of the transformed bacteria, which will contain replications of each strand of the phage, are plated in agar to obtain plaques. Theoretically 50% of the new plaques will contain phage having as a single strand the mutated form; 50% will have the original sequence. Replicates of the plaques are hybridized to kinased synthetic probe at temperatures and conditions which permit hybridization with the correct strand, but not with the unmodified sequence. The thus identified, desired, modified sequences are then recovered and cloned to serve as sources for the desired DNA.

C.5. Hybridization with Probe

DNA libraries are probed using the procedure of Grunstein and Hogness (*Proc Natl Acad Sci* (USA) (1975) 73:3961). Briefly, in this procedure, the DNA to be probed is immobilized on nitrocellulose filters, denatured, and prehybridized with a buffer containing 0–50% formamide, 0.6M NaCl, 60 mM sodium citrate, 0.02% (wt/v) each of bovine serum albumin, polyvinyl pyrollidine, and Ficoll, 50 mM sodium phosphate (pH 6.5), 1% glycine, and 100 μg/ml carrier denatured DNA. The percentage of formamide in the buffer, as well as the time and temperature conditions of the prehybridization and subsequent hybridization steps depends on the stringency desired. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, e.g. about 40°–42° and a high percentage, e.g. 50% formamide. Following prehybridization, this same buffer, now containing the $^{32}P$ kinased oligonucleotide probe, is added to obtain hybridization. Radioautography of the treated filters shows the location of the hybridized probe, and the corresponding locations on replica filters which have not been probed can then be used as the source of the desired DNA.

C.6. Verification of Construction and Sequencing

For routine vector constructions, ligation mixtures are transformed into *E. coli* strain HB101 or other suitable host, and successful transformants selected by antibiotic resistance or other markers. Plasmids from the transformants are then prepared according to the method of Clewel, D.B., et al, *Proc Natl Acad Sci* (USA) (1969) 62:1159, usually following chloramphenicol amplication (Clewell, D.B., *J Bacterior* (1972) 110:667). The isolated DNA is isolated and analyzed by restriction analysis, or sequenced by the dideoxy method of Sanger, F., et al, *Proc Natl Acad Sci* (USA) (1977) 74:5463, as further described by Messing, et al, *Nucleic Acids Res* (1981)9:309, or by the method of Maxam, et al, *Methods in Enzymology* (1980) 65:499.

D. Examples

The following examples are intended to illustrate but not limit the invention. The procedure set forth, for example, in paragraphs D.1 and D.2 may, if desired, be repeated but need not be, as techniques are available for construction of the desired nucleotide sequences based on the information provided by the invention. Expression is exemplified in *E. coli* and in yeast, however other systems are available as set forth more fully in paragraph C.1. Additional epitopes derived from the genomic structure may also be produced, and used to generate antibodies as set forth below.

D.1. Preparation of cDNA

D.1.a. Production of BVD Virus

Bovine Embryonic Kidney cells (BEKI) cells were grown in MEM (Earl's) containing 0.85 g/l $NaHCO_3$ and 10% or irradiated fetal calf serum. The biologically cloned Osloss strain of BVD virus was passaged 5 times through BEJKI cells at a multiplicity of 0.1. Cytopathic effects, consisting of clustering of cells followed by vacuolation and then cell lysis, were readily observable from the first passage. Final titers (~$10^8$ pfu/ml) were obtained after recovery of virus by freezing and thawing of infected cells.

For the virus production, 175 $cm^2$ plastic flasks of subconfluent BEKI cells were used. The cells were washed 3 times with infection buffer (MEM (Earl's) +2.2 g/l $NaHCO_3$, pH 7.6) and then were infected with 2 ml of BVD in infection buffer at a multiplicity of 0.05 pfu/cell. After 1 hr at 35° C., 18 ml of infection buffer was added and the cells were incubated for 4–5 days at 35° C., after which cytopathic effect (vacuolation followed by cells lysis) was greater than 80%. In a typical production, 150 flasks of cells were infected. The medium (about 3 liters) was collected and stored at 4° C. The remaining cells were scraped in 2 ml of infection buffer/flask, subjected to 3 cycles of freezing and thawing, nd the final suspension was added to the infection medium. After a centrifugation at 10,000 g for 30 min, the supernatant was concentrated 10-fold by ultracentrifugation at 120,000 g for 4 hrs and 40 min at 4° C.

Infectious virus had a density of 1.12 g/ml as measured by isopicnic banding in sucrose density gradient, and appeared as 45–55 nm spherical particles by electron microscopy. The virus preparations were neutralized by anti-BVD antiserum from rabbits injected with virus or from bovines.

D.1.b. Extraction and Purification of Viral RNA

RNA was isolated from the virus pellet by the CsCl/guanidinum thiocyanate method as described by Chirgwin, et al, *Biochemistry* (1979) 18:3294, and the purified RNA stored in 70% ethanol at −20° C. This RNA preparation contained a large amount of contaminating low molecular weight cellular RNA and intact viral RNA. Viral RNA was further purified by sucrose density gradient centrifugation as follows:

An aliquot containing an estimated amount of 5 μg of BVD-RNA was centrifuged at 10,000 g for 15 min at 4° C. The pellet was washed with 80% ethanol, denatured in 375 μl of 99% DMSO (99%), 5 mM Tris-HCl (pH 7.5) and incubated for 5 min at 37° C. After addition of 1.125 ml of 5 mM Tris HCl (pH 7.5), 1 mM EDTA, 1% Sarkosyl, the solution was heated for 2 min at 70° C. and quenched on ice. This solution was distributed on 5×15-30% sucrose gradients in 5 mM Tris HCl (pH 7.5), 10 mM EDTA, 0.1M NaCl, 1% Sarkoxyl (in sterile siliconized Beckman SW40 tubes). A sixth gradient was loaded with 3′ end labeled RNA as a marker (see below). After a centrifugation for 16 hrs at 19,000 rpm (20° C.), the gradients were fractionated (1 ml fractions). The RNA from each fraction of the gradient corresponding to that containing marker-labeled RNA was precipitated with 2.5 volumes of ethanol in the presence of carrier yeast RNA (10 μg) and subjected to formaldehyde agarose gel electrophoresis, Lehrach, et al, *Biochemistry* (1977) 16:4743, to determine which fraction contained the BDV-RNA band. Fractions corresponding to those containing the BDV-RNA, were pooled from the parallel gradients and precipitated with 2.5 volumes of ethanol, washed with 80% ethanol and stored at −20° C. in 70% ethanol.

The purified viral RNA was labeled with $^{32}P$-pCp (3000 Ci/n mol) according to England, et al, *Meth Enzymol* (1980) 65:65–74, and analyzed by agarose gel electrophoresis in the presence of 22M formaldehyde as described in Lehrach, et al. (supra). Fluorography was done with $^{3}H$-Enhancer (NEN) as recommended by the manufacturer.

The majority of the radioactivity was associated with low molecular weight RNA (less than 2 kb), but a small proportion was found in a high molecular band approximately 12.5 kb, identified as RNA by labeling properties with RNA ligase, its sensitivity to RNAse and alkali, and resistance to DNAse and proteinase K. In agreement with other reports on togaviruses of the flavivirus group, the BDV-RNA did not bind to oligo dT cellulose, showing either the absence of a polyA stretch at eh 3′ end, or that, if present, the polyA is extremely short.

Control Sindbis virus RNA was properly retained by the same column.

These properties of eh 12.5 kb band were identical with those shown by RNA extracted from BEKI cells, grown as follows:

BEKI cells were grown in 25 $cm^2$ plastic flasks, washed 3 times with infection buffer, and infected at multiplicities of 50–100 pfu/cell with 1 ml of BDV solution. After one hour at 35° C., 4 ml of infection buffer was added and the incubation was continued. After 12, 15, 18, 21 and 36 hrs (36 hr corresponds to a complete cycle of BDV replication), the newly synthesized RNA was labeled with $^3$H-uridine (100 μci/dish). Uninfected cellular RNA harvested after 18 hrs of incubation was also analyzed. After 30 min of labeling, the cellular RNA was extracted using the CsCl/guanidinium thiocyanate method of Chirgwin et al, 1979 (supra). The pellet of RNA, obtained after ultracentrifugation through a 5.7M CsCL cushion, was directly analyzed by formaldehyde agarose gel electrophoresis and gel was dried and fluorographed. In all the incubation times tested, a 12.5 kb band which is absent in the uninfected cells could be detected which has the same physico-chemical properties as shown by the RNA above.

D.1.c. Preparation of cDNA

The viral RNA isolated from the virus in paragraph D.1.b. was polyadenylated using the method of Sippel, *Eur J Biochem* (1973), 37:31–40. Briefly, the estimated amount of 0.7 μg of purified BVD RNA was incubated in 5 ml of 5 mM methylmercury hydroxide for 10 min at room temperature and incubated for 6 min at 37° C. with 20 units of polyA polymerase (BRL and 500 μCi of $^3$H-ATP (36 Ci/mmol, Amersham) in 50 μl of 50 mM HCl (pH 7.5), 10 mM $MgCl_2$, 2.5 mM $MnCl_2$, 0.3M NaCl, 1.5 mM 2-mercaptoethanol and containing 2.5 μg of RNAse-free BSA and 5 units of human placental ribonuclease inhibitor (BRL). After phenol/chloroform extraction, the RNA was purified by chromatography on Sephadex G50 and precipitated with 2.5 volumes of ethanol. The polyA RNA was used to prepare probes and as a template for the cDNA library.

To make probes 1 μg of the polyA RNA was incubated for 10 min at room temperature in 5 μl of 10 mM methylmercury hydroxide and then 45 min at 37° C. with 40 units of reverse transcriptase in 100 ml of 50 mM Tris HCl (ph 8.3). 10 mM $MgCl_2$. 1.5 mM 2-mercaptoethanol, 1 mM dATP, dGTP and dTTP, 10 μM dCTP, 0.2 mg/ml of actinomycin D. 5 units of human placental ribonuclease inhibitor, 500 μCi of alpha $^{32}$P-dCTP (3000 Ci/mmole, Amersham) and 20 μg of oligonucleotides obtained by partial digestion with DNAse I of calf thymus DNA (random primers). After 15 and 30 min, ten more units of reverse transcriptase were added. After phenol/chloroform extration and Sephadex G50 column chromatography the RNA was hydrolyzed with 0.1M NaOH (1 hr at 65° C.) thus yielding single stranded cDNA strands. The solution was neutralized with 0.1M acetic acid and added directly to the hybridization buffer.

For the cDNA library two separate cloning protocols involving dT (12-18) primers or random (calf thyus), DNA-derived oligonucleotide primers were used. RNA polyadenylated in vitro as described above was used. Approximately 1 μg polyadenylated RNA was incubated with 10 mM methylmercury hydroxide in a 10 μl volume for 10 min at room temperature, and excess reagent was titrated by adding 1 μl of a 3M 2-mercaptoethanol solution. This denatured polyA RNA was used immediately in the presence of 50 mM Tris pH 8.0. 1 mM dATP, dGTP, dCTP and dTTP, 2.5 μg/ml dT12-18 or the calf thymus random oligonucleotide primers, 10 mM $MgCl_2$, 10 μg/ml actinomycin D, 100 units of RNAse inhibitor (BRL) and 60 units of reverse transcriptase in a total volume of 100 μl.

The samples were diluted to 400 μl with a buffer containing 10 mM Tris pH 7.0, 100 mM NaCl, 10 mM EDTA and 0.2% SDS extracted with phenol/-chloroform, freed of dNTPs by Sephadex G50 chromatography, and ethanol precipitated.

The precipitated mixture of RNA and cDNA hybrids (10 μl) were diluted into 50 ml of S1 buffer (500 mM NaCl, 50 mM NA acetate pH 4.5 and 1 mM $ZnCl_2$ and digested for 15 min at room temperature with 20 units of Sl nuclease. The reaction was stopped by diluting the sample to 500 ml with a buffer containing 50 mM NaCl, 10 mM EDTA and 50 mM Tris pH 7.0, and digestion was continued for 15 min at room temperature by adding 20 μg/ml of RNAse A. After phenol and chloroform extraction, the RNA:cDNA hybrids were concentrated by ethanol precipitation and fractionated on a Sepharose CL4B column prepared in a 1 ml plastic pipette. The excluded peak, containing molecules larger than 800 base-pairs, was pooled and ethanol precipitated to give 50 ng of hybrid for the dT primed, and 200 ng of hybrid for he random claf thymus fragment primed reactions.

Both samples were tailed for dC residues under conditions yielding 15–25 residues per DNA or RNA termini, and annealed to a dG tailed pBR322 vector linearized at the PstI site (NEN) at a vector concentration of 0.1 μg/ml. The annealed plasmids were transformed into *E. coli* HB101 to Amp® to obtain the cDNA library.

D.2. Screening of the cDNA Library

Screening employed a+/−method using labeled cDNAs prepared from RNA isolated from uninfected BEKI cells (−probe) and from RNA isolated from the virus obtained after complete lysis of the cells (+probe). Colonies of the *E. coli* harbored cDNA library were grown, lysed on nitrocellulose filters (two replicas) and probed. The hybridization buffer used for +probe also contained an excess of cellular RNA isolated from uninfected BEKI cells (10 mg/ml). The colonies which gave a clear signal with the +probe and no response with the −probe were selected. By this method, 95 oligo dT-primed and 185 random primer primed clones were selected. The length of the inserts after PstI digestion varied from 400 to 4,000 base pairs. No full-length virus specific cDNA was obtained.

One of the clones, pDT28, with a 880 bp insert was selected for further analysis. This fragment from a PstI digest of plasmid DNA was purified by acrylamide gel electrophoresis, digested with DdeI and MboI and then labeled with the Klenow fragment of DNA polymerase I and the four $^{32}$P dNTPs to yield $10^6$–$10^4$ cpm/mg of insert. Labelled insert was verified by hybridization to viral RNA fractionated on a 0.9% agarose gel electrophoresis in presence of formaldehyde (Smiley, et al, *Anal Biochem* (1983) 131:365–372). Stringent hybridization conditions were used: prehybridizations and hybridizations were overnight at 42° C., and 50% formamide was used in hybridizations. Washing was at 65° C. first with 2xSSC, 0.1% SDS and then with 0.2xSSC and 0.1% SDS.

In the foregoing verification, RNA from uninfected cells was used as negative control. The absence of exogenous viral sequences in the genome of the cells was verified by failure of cellular DNA digested with BamHI and EcoRI to bind to pDT28 probe in Southern blot analysis. The RNA from infected cells after 24 hrs of infection at a multiplicity greater than 1, and from the pellet of virus after complete cell lysis were used as positives. No hybridization was detected with the RNA from the uninfected cells, but the inserts hybridized to an approximately 13 kb band of the RNA isolated from the infected cells or from the pellet of virus.

The plasmid pDT28, which had been verified to contain a PstI insert which binds to the viral RNA, was used to probe the cDNA library for additional clones, and the entire sequence was recovered by "walking" techniques. In this way, eight additional plasmids were recovered which span the entire 12.5 kb genome of the virus. The positions of the overlapping inserts are shown in FIG. 1. As shown in FIG. 1, the pDT28 clone occupies a roughly central portion of the genome. The 8 additional plasmids recovered from the cDNA library in a manner analogous to that described above, but using the appropriate overlapping sequence-containing clone as probe, were grown in *E. coli*, and the plasmid DNA isolated. The inserts were sequenced, and verified to contain overlapping portions. The results of this sequencing are shown in FIG. 2, which provides the entire genomic RNA sequence ascertained from the inserts.

The orientation shown in FIG. 2 was determined by subcloning pDT28 into M13 into both orientations, labeling the resultant phage, and using the labeled phage as a probe against RNA known to be of positive polarity. This was done by spot hybridization on nitrocellulose filters using uninfected cell RNA, infected cell RNA, and template viral RNA. The infected cell RNA and template RNA should be of positive polarity. Therefore, the M13 orientation hybridizing to infected cell RNA and viral RNA contains a negative sense strand, and from this information, the 5' to 3' sequence of inserts from pCT63 to pCT185 could be deduced.

This conclusion was confirmed by analysis of the sequence of pCT63, which indicates its capability to form the expected hairpin structure at the 5' end, and by the absence of additional clones in the cDNA library having additional 5' sequences to that of pCT63.

D.3. Expression of Sequences Encoding BGal-BDV Fusions in *E. coli*

Twelve portions of the BDV genome were obtained as follows: (1) the entire cDNA sequences per se, (2) products of restriction cleavage (with PstI or BamHI or both) of the foregoing cDNAs, and (3) a ligated sequence obtained by ligating the pCT185 cDNA with a fragment of another. (See the table below). These portions were used to encode the BDV portions of the fusion proteins. These eleven BDV protein encoding sequences were cloned into one of or a mixture of pUR290, pUR291, and pUR292, which contain restriction sites, e.g., BamHI and PstI sites in all three possible reading frames with the $\beta$-gal codons, so as to encode fusion proteins at the C-terminal portion of the $\beta$-galactosidase protein (Ruther, U., et al, *Embo J* (1980) 2:1791-1794). Since all three possible reading frames are provided for the restriction sites used, the correct reading frame in at least one of the vectors for the fusion protein is assured. Table 1 summarizes the vectors prepared and the BDV sequence contained in each. Nucleotide numbers are as indicated in FIG. 2.

TABLE 1

| Name | pUR Parent | BDV Insert Derived from | BDV Nucleotides Contained in pUBVD Vectors (Numbers as in FIG. 2) |
|---|---|---|---|
| pUBVD1 | pUR290 | pCT63 | 1397-2607 |
| pUBVD2 | pool | pCT36 | 2037-2574 |
| pUBVD4 | pUR292 | pCT183 | 2955-4560 |
| pUBVD5 | pool | pDT28 | 5650-6450 |
| pUBVD6 | pUR290 | pCT174 | 7225-10718 |
| pUBVD7 | pool | pCT174 | ~9500-10811 |
| pUBVD8 | pUR292 | pDT65 | 10442-10811 |
| pUBVD9 | pUR292 | pDT65 + pCT185 | 10442-12470 |
| pUBVD10 | pUR290 | pCT185 | 11030-12457 |
| pUBVD11 | pUR290 | pCT185 | 11405-12457 |
| pUBVD12 | pUR291 | pCT63 | 597-1397 |
| pUBVD13 | pUR290 | pDT28 + pDT17 | ~6000-~7800 |

Each of the twelve cDNA sequences was mixed with T4 ligase in the presence of PstI-digested mixtures of pUR290, 291, and 292 (or of one of these if the correct reading frame was deduced) and the ligation mixture transformed into *E. coli* strain D1210 (LacI$^-$mutant of HB101) to Amp ®. Successful transformants were confirmed by hybridization with labeled insert, and isolated plasmid DNA was analyzed by restriction analysis to confirm correct orientation. Expression was induced in successful transformants containing correctly oriented inserts by treating with IPTG (1 mM) on L-broth medium containing 40 $\mu$g/ml ampicillin. Three hours after induction, the cells were harvested, and lysed by sonication. The fusion proteins were produced as inclusion bodies, and the inclusion bodies were harvested by the method of Klempnauer, et al, *Cell* (1983) 33:345-355, and stored at $-20°$ C. suspended in 10 mM Tris (pH 8.0), 1 mM EDTA. Approximately 10-30 mg inclusion body proteins were obtained per ml of culture.

D.4. Characterization of the Fusion Proteins

The fusion proteins were characterized as to their antigenic properties both in insoluble and solubilized forms.

Inclusion body proteins solubilized in 1% SDS or 7M urea followed by dialysis to a final concentration of 1 mg/ml are unreactive with sera from infected claves or from rabbits infected with purified virus.

Preparation of Antisera. Both solubilized and unsolubilized inclusion bodies were injected into rabbits using peri-lymph nodal immunizations with 500 $\mu$g protein emulsified with Freund's complete adjuvant, with boosting every 4 weeks (IM injection of 500 $\mu$g emulsified in adjuvant) and bled 10 days after boost. Control antisera were prepared from infected claves or from rabbits injected with purified virus. The antisera were tested for immunoactivity by ELISA and immunofluorescence, and by Western blot and immunoprecipitation.

Western blot and immunoprecipitation yield complementary information with respect to reactivity. In immunoprecipitation, the native protein mixture is reacted with the test serum and the immunoprecipitate subjected to SDS-PAGE. Therefore, immunoprecipitation assesses immunoreactivity with the native protein.

However, in the Western blot procedure SDS, PAGE is performed before the antisera are tested for precipitation with the proteins on the gel. Therefore, Western blot assesses reactivity with denatured protein.

The results of these procedures are given below.

Results. The control antisera were immunoreactive with respect to proteins extracted from the virus pellet produced on BEKI cells, and showed immunoprecipitation with the 76 kD protein presumed to be the major antigenic component, as well as minor components presumed to be, at least in part, virion proteins having molecular weights of 36, 43, 47, 51 and 56 kD. No immunoprecipitation occurred when the control antisera were tested on Western blot. Control antisera against infection thus react with antigens in the native protein, but not after denaturation.

Immunoprecipitation and Western Blot. Most of the antisera formed in response to the fusion proteins were negative both in assay by immunoprecipitation and, like the control antisera, on Western blot.

However, there were exceptions. The antiserum generated by fusion protein 7 immunoprecipittes the 36 kD protein from BEKl-grown virus and reacts by Western blot to the 76 kD and 51 kD bands. Antiserum from fusion 5 immunoprecipittes 3 sizes of proteins: 64, 98, and 105 kD, sizes not precipitated by control antisera. Antiserum from fusion 9 precipitates a 58 kD band, also not precipitated by the control antisera. The significance of MW of the materials is not clear since it is not clear which, if any, of these proteins represent glycosylated materials with corresponding alterations in molecular weight.

ELISA (carried out according to the procedure of Bartlett, et al, in *Protides of the Biological Fluids,* H. Peeters, e., Pergamon Press, Oxford, 1976, 24:767–770) used partially purified virus as antigen. Only the antiserum prepared against fusion protein 7 was positive at a 1:40 titer; serum prepared against fusion proteins 5 and 11 had titers of 1:4 and 1:8, respectively. Nonimmune sera were negative.

Immunofluorescence was conducted using labeled live or fixed infected cells. The antiserum prepared against fusion protein 11 was slightly positive in immunoreactivity with live cells; on cells fixed with methanol, acetone, or formaldehyde, serum prepared from fusion protein 7 gave the same strong response as control antisera from the infected animals, whereas antisera 5 and 3 were weakly positive against proteins extracted from the virus pellet produced on BEKI cells.

We claim:

1. Am isolated and purified recombinant DNA fragment which encodes at least one viral polypeptide encoded by the BDV genomic sequences shown in FIG. 2.

2. The DNA fragment of claim 1 which is nucleotides 9500–10811 in FIG. 2.

3. A recombinant expression system functional in a compatible host cell, to effect the production of a BDV protein, which expression system comprises:

an open reading frame within the DNA sequence of FIG. 2 or a degenerate DNA sequence encoding the same protein.

4. The expression system of claim 3 wherein said open reading frame is that of nucleotides 9500–10811 in FIG. 2.

5. A recombinant expression system comprising:

a coding portion consisting essentially of a DNA that encodes BDV protein or a portion thereof encoded by the DNA sequence of FIG. 2, wherein said DNA is operably linked to a control sequence functional in a compatible host.

6. The expression system of claim 5 wherein said coding portion consists essentially of nucleotides 9500–10811 in FIG. 2.

7. The system of claim 5 which further includes upstream of said coding portion, and in reading frame therewith, a fused DNA sequence encoding a protein or portion thereof native to the recombinant host.

8. A recombinant host cell transformed with the expression system of claim 3.

9. A recombinant host cell transformed with the expression system of claim 5.

10. A probe useful in detecting the BDV genome, which probe comprises a portion of the nucleotide sequence of FIG. 2 effective to hybridize to said genome.

* * * * *

UNITED STATES PATENT AND TRADEMARK OFFICE

CERTIFICATE OF CORRECTION

PATENT NO. : 5,206,163

DATED : April 27, 1993

INVENTOR(S) : Andre Renard, Dino Dina and Joseph Martial

It is certified that error appears in the above-indentified patent and that said Letters Patent is hereby corrected as shown bel :

Title page item [73],

Please add to the Assignee names: Region Wallonne

The Assignee names will read as follows:

Chiron Corporation, Emeryville, Calif. and
Region Wallonne, Jambes, Belgium

Signed and Sealed this

Nineteenth Day of August, 1997

Attest:

BRUCE LEHMAN

Attesting Officer

*Commissioner of Patents and Trademarks*